United States Patent
Ezaka et al.

(10) Patent No.: US 8,523,642 B2
(45) Date of Patent: Sep. 3, 2013

(54) GASEOUS CONSTITUENT SUPPLY DEVICE

(75) Inventors: Tomohisa Ezaka, Kariya (JP); Manabu Maeda, Nagoya (JP); Takurou Kawaguchi, Kariya (JP)

(73) Assignee: Denso Corporation, Kariya (JP)

( * ) Notice: Subject to any disclaimer, the term of this patent is extended or adjusted under 35 U.S.C. 154(b) by 1953 days.

(21) Appl. No.: 11/712,354

(22) Filed: Feb. 28, 2007

(65) Prior Publication Data

US 2007/0261438 A1  Nov. 15, 2007

(30) Foreign Application Priority Data

Mar. 3, 2006 (JP) ................ 2006-058285
Mar. 27, 2006 (JP) ................ 2006-086198
Mar. 28, 2006 (JP) ................ 2006-087865
Mar. 28, 2006 (JP) ................ 2006-087872
May 23, 2006 (JP) ................ 2006-143206
Jul. 4, 2006 (JP) ................ 2006-184807

(51) Int. Cl.
*B60H 3/00* (2006.01)
*B01F 3/04* (2006.01)

(52) U.S. Cl.
USPC ............................ 454/156; 261/30

(58) Field of Classification Search
USPC .......................................... 454/156
See application file for complete search history.

(56) References Cited

U.S. PATENT DOCUMENTS

2006/0222672 A1  10/2006  Ezaka et al.

FOREIGN PATENT DOCUMENTS

| JP | 02-71544 | 5/1990 |
|---|---|---|
| JP | 06-032144 | 2/1994 |
| JP | 07-332750 | 12/1995 |
| JP | 08-071409 | 3/1996 |
| JP | 09-122220 | 5/1997 |
| JP | 11-011308 | 1/1999 |
| JP | 2000-176339 | 6/2000 |
| JP | 2004-053102 | 2/2004 |
| JP | 2004-298607 | 10/2004 |
| JP | 2005-102719 | 4/2005 |
| JP | 2005-202599 | 7/2005 |
| JP | 2005-296540 | 10/2005 |
| JP | 2006-282085 | 10/2006 |
| JP | 2006-305484 | 11/2006 |

OTHER PUBLICATIONS

Office Action dated Apr. 13, 2010 in Japanese Application No. 2006-086198 with English translation thereof.
Office Action dated Dec. 7, 2010 in Japanese Application No. 2006-184807 with English translation thereof.

*Primary Examiner* — Steven B McAllister
*Assistant Examiner* — Helena Kosanovic
(74) *Attorney, Agent, or Firm* — Harness, Dickey & Pierce, PLC

(57) ABSTRACT

A gaseous constituent supply device for supplying an air vortex ring containing a gaseous constituent includes a first chamber for holding the gaseous constituent, a compressing portion for compressing air in the first chamber, and a second chamber communicating with the first chamber through an opening. The second chamber holds the gaseous constituent therein. The air vortex ring is generated in the second chamber such that air blown from the first chamber into the second chamber through the opening takes in the gaseous constituent in the second chamber. The second chamber has an emitting outlet, through which the generated air vortex ring is emitted, and the emitting outlet is provided opposite to the opening.

14 Claims, 27 Drawing Sheets

GASEOUS CONSTITUENT SUPPLY DEVICE

CROSS REFERENCE TO RELATED APPLICATION

This application is based on Japanese Patent Applications No. 2006-184807 filed on Jul. 4, 2006, No. 2006-86198 filed on Mar. 27, 2006, No. 2006-87865 filed on Mar. 28, 2006, No. 2006-87872 filed on Mar. 28, 2006, No. 2006-58285 filed on Mar. 3, 2006, No. 2006-143206 filed on May 23, 2006, the disclosures of which are incorporated herein by reference in its entirety.

BACKGROUND OF THE INVENTION

1. Field of the Invention

The present invention relates to a gaseous constituent supply device for supplying air containing a predetermined gaseous constituent. For example, the device is suitably used for a vehicle.

2. Description of Related Art

A gaseous constituent supply device disclosed in JP-A-2004-298607 blows and emits an air cannon projectile (e.g., air vortex ring) containing a perfume constituent. In the device, the perfume constituent is stored in a perfume unit, and supplied to a case from the perfume unit through a duct. When a compressing portion for compressing air in the case is actuated, air is blown from the case through an outlet of the case. Then, a shearing force is generated between the blown air and ambient air around the outlet. Thereby, the ambient air is sucked into the blown air. Thus, the air vortex ring can be formed into a ring shape.

However, because the ambient air is sucked into the air vortex ring, a concentration of the perfume constituent in the air vortex ring is lower than that in the case. Therefore, the concentration of the perfume constituent in the air vortex ring cannot be kept higher, even when the concentration of the perfume constituent in the case is made higher. That is, the air vortex ring containing a high concentration of the gaseous constituent cannot be supplied.

Further, in order to supply the perfume constituent into the case from the perfume unit, outside air is introduced into the perfume unit. Then, the outside air is made to contain the perfume constituent, and supplied to the case. Therefore, the concentration of the perfume constituent in the case is difficult to be made higher. That is, a high concentration of the perfume constituent cannot be supplied to a compartment of a vehicle. Furthermore, a size of the device may be larger, because the perfume unit and the case are separately disposed in the device.

A gaseous constituent supply device disclosed in JP-A-2000-176339 blows and emits an air cannon projectile (e.g., air vortex ring) containing a perfume constituent. In the device, a membrane-shaped compressing portion is disposed opposite to an outlet for emitting the air vortex ring through a pressure room holding a predetermined gaseous constituent. When the compressing portion is displaced toward the outlet, air containing the gaseous constituent in the pressure room is compressed. Therefore, the air cannon projectile containing the gaseous constituent can be emitted outward. The compressing portion is integrated with a pair of a magnet and a coil. When driving current (electricity) is supplied to the coil, a Lorentz force is generated so as to make the compressing portion to be displaced toward the outlet. The driving current is a rectangular-wave current.

However, when the driving current is supplied to the coil, the displacement of the compressing portion does not sufficiently respond to the rectangular wave, as shown in FIG. 42. Thereby, a transient distortion of the compressing portion may be generated relative to a target position. The transient distortion represents vibrations of the compressing portion. The transient distortion may generate noise, which is uncomfortable for occupants in the vehicle.

Further, the compressing portion has a compressing face for compressing air containing the gaseous constituent in the pressure room. The compressing face may have a concave shape relative to the outlet. When the compressing portion is displaced toward the outlet, the compressing face compresses air in the pressure room.

The compressing portion instantaneously compresses air in the pressure room, in order to emit the air cannon projectile. However, the instantaneous displacement of the compressing portion may generate impact noise toward occupants in the vehicle. Further, when the compressing face has the concave shape relative to the outlet, a directional angle of the impact noise is small. Thereby, the air cannon projectile may have a directional tendency (characteristic). Thus, the impact noise may have a high sound pressure, and the high sound pressure may be excessively transmitted to the occupants.

A gaseous constituent supply device disclosed in JP-A-2004-298607 includes a compressing portion, a perfume unit, a case and a duct. The compressing portion compresses air in the case. The perfume unit holds a perfume constituent therein. The duct is disposed between the perfume unit and the case, in order to supply the perfume constituent from the perfume unit to the case. The compressing portion compresses air containing the perfume constituent in the case, in order to emit an air mass containing the perfume constituent.

However, a size of the device may be large, because the compressing portion and the perfume unit are separately disposed in the device. Further, an electromagnetic valve of the duct has to be controlled, in order to mix the perfume constituent into air in the case.

SUMMARY OF THE INVENTION

In view of the foregoing and other problems, it is a first object of the present invention to provide a gaseous constituent supply device, which can supply an air vortex ring containing a high concentration of a gaseous constituent. It is a second object of the present invention to provide a small-size gaseous constituent supply device. It is a third object of the present invention to provide a gaseous constituent supply device, which generates less noise. It is a fourth object of the present invention to provide a gaseous constituent supply device, which generates less impact noise.

According to a first example of the present invention, a gaseous constituent supply device for supplying an air vortex ring containing a gaseous constituent includes a first chamber, a compressing portion and a second chamber. The first chamber holds the gaseous constituent therein, and has an opening, through which air containing the gaseous constituent is blown. The compressing portion compresses air in the first chamber so as to blow air from the first chamber through the opening. The second chamber communicates with the first chamber through the opening. The second chamber holds the gaseous constituent therein, and has an emitting outlet provided opposite to the opening of the first chamber. The second chamber generates the air vortex ring by air blown from the first chamber through the opening while taking in the gaseous constituent. The second chamber emits the generated air vortex ring through the emitting outlet.

Accordingly, the device can supply the air vortex ring containing a high concentration of the gaseous constituent.

According to a second example of the present invention, a gaseous constituent supply device for supplying an air cannon projectile containing a gaseous constituent to a compartment of a vehicle includes a case, a compressing portion, a gaseous constituent generator and a circulating portion. The case defines therein a gaseous constituent chamber holding the gaseous constituent therein and having an emitting part, through which the air cannon projectile is emitted from the case. The compressing portion compresses air in the chamber so as to emit the air cannon projectile through the emitting part. The gaseous constituent generator generates the gaseous constituent. The circulating portion circulates air in the case between the chamber and the generator.

Accordingly, a size of the device can be effectively reduced.

According to a third example of the present invention, a gaseous constituent supply device for supplying an air cannon projectile containing a gaseous constituent to a compartment of a vehicle includes a gaseous constituent chamber, a compressing portion, a driving portion and a restricting portion. The gaseous constituent chamber holds the gaseous constituent therein, and has an emitting part, through which the air cannon projectile is emitted from the chamber into the compartment. The compressing portion compresses air containing the gaseous constituent in the chamber so as to emit the air cannon projectile through the emitting part. The compressing portion is disposed to be displaced from a reference position to a compression position. The driving portion includes a magnet and a coil, in which the coil is supplied with a driving current so as to generate a Lorentz force for displacing the compressing portion. The restricting portion restricts the compressing portion toward the reference position, when the compressing portion is displaced toward the compression position.

According to a fourth example of the present invention, a gaseous constituent supply device for supplying an air cannon projectile containing a gaseous constituent to a compartment of a vehicle includes a gaseous constituent chamber, a compressing portion and a driving portion. The gaseous constituent chamber holds the gaseous constituent therein, and has an emitting part, through which the air cannon projectile is emitted from the chamber. The compressing portion compresses air containing the gaseous constituent in the chamber so as to emit the air cannon projectile through the emitting part. The compressing portion is disposed to be displaced from a reference position to a compression position. The driving portion includes a magnet and a coil, in which the coil is supplied with a driving current so as to generate a Lorentz force for displacing the compressing portion. The driving current has a main pulse for emitting the air cannon projectile, and a brake pulse for braking the compressing portion.

According to a fifth example of the present invention, a gaseous constituent supply device for supplying an air cannon projectile containing a gaseous constituent to a compartment of a vehicle includes a gaseous constituent chamber, a compressing portion and a driving portion. The gaseous constituent chamber holds the gaseous constituent therein, and has an emitting part, through which the air cannon projectile is emitted from the chamber. The compressing portion compresses air containing the gaseous constituent in the chamber so as to emit the air cannon projectile through the emitting part. The compressing portion is disposed to be displaced from a reference position to a compression position. The driving portion includes a magnet and a coil, in which the coil is supplied with a driving current so as to generate a Lorentz force for displacing the compressing portion. The driving current is changed in a wave shape having a rising part and a falling part in accordance with time. The compressing portion is displaceable so as to be synchronized with the wave shape.

According to the third, fourth and fifth examples, the device can have less noise.

According to a sixth example of the present invention, a gaseous constituent supply device for supplying an air cannon projectile containing a gaseous constituent to a compartment of a vehicle includes a gaseous constituent chamber and a compressing portion. The gaseous constituent chamber holds the gaseous constituent therein, and has an emitting part, through which the air cannon projectile is emitted from the chamber. The compressing portion has a compression face for being displaced toward a compression side from a reference position so as to compress air in the chamber and emit the air cannon projectile through the emitting part. The compression face has a protrusion shape protruding toward the compression side, when the compressing portion is in the reference position.

Accordingly, the device can have less impact noise.

According to a seventh example of the present invention, a gaseous constituent supply device for supplying an air mass containing a gaseous constituent to a compartment of a vehicle includes a case, a compressing portion, a communication part and a controlling unit. The case defines a first chamber holding the gaseous constituent therein, and a second chamber having an emitting part, through which the air mass is emitted into the compartment from the second chamber. The compressing portion compresses air in the second chamber so as to emit the air mass. The compressing portion is located in the case to separate the first chamber and the second chamber from each other. The communication part makes the first chamber and the second chamber to communicate with each other. The controlling unit which controls compressing operation of the compressing portion such that the gaseous constituent flows from the first chamber into the second chamber through the communication part.

According to an eighth example of the present invention, a gaseous constituent supply device for supplying an air mass containing a gaseous constituent to a compartment of a vehicle includes a case, a communication part and a movable portion. The case defines a first chamber holding the gaseous constituent therein, and a second chamber having an emitting part, through which the air mass is emitted into the compartment from the second chamber. The communication part communicates the first chamber and the second chamber. The movable portion is movable toward the first chamber to decrease a volume of the first chamber, or toward the second chamber to decrease a volume of the second chamber. The movable portion is moved to the first chamber such that the gaseous constituent is supplied to the second chamber from the first chamber through the communication part.

According to the seventh and eighth examples, a size of the device can be reduced.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF PREFERRED EMBODIMENT

First Embodiment

A first embodiment will be described with reference to FIGS. 1-4. A gaseous constituent supply device emits an air vortex ring F containing a predetermined gaseous constituent, and is typically mounted to a vehicle 1. The device is constructed with emitting units 10A, 10B, 10C, which are provided in a compartment 2 of the vehicle 1, in order to supply the gaseous constituent to each occupant 3, 4.

Figure 1:
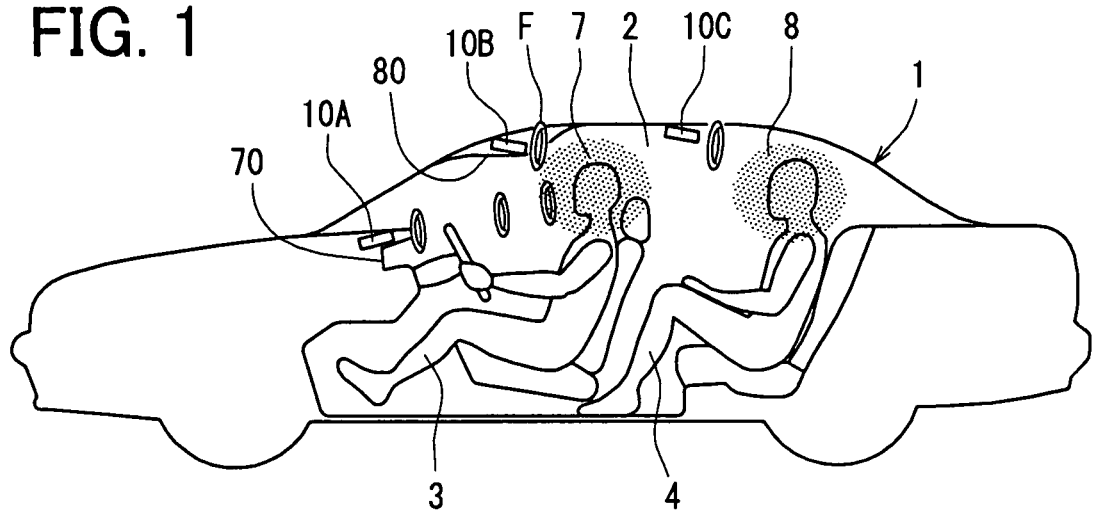
FIG. 1 is a schematic diagram showing an arrangement of emitting units of a gaseous constituent supply device in a first embodiment of the present invention.

As shown in FIG. 1, the emitting units 10A, 10B are positioned such that the air vortex ring F can be emitted toward the occupant 3, and the emitting unit 10C is positioned such that the air vortex ring F can be emitted toward the occupant 4. Specifically, the emitting unit 10A is disposed in an instrument panel 70, and the emitting unit 10B is disposed in an overhead module 80 on a front seat side ceiling part. The emitting units 10A, 10B emit the air vortex ring F toward the occupant 3. In contrast, the emitting unit 10C is disposed on a rear seat side ceiling part, and emits the air vortex ring F toward the occupant 4. When the air vortex ring F hits a body, e.g., face or shoulder, of the occupant 3, 4, a mass of the air vortex ring F collapses, and the gaseous constituent contained in the air vortex ring F diffuses in a diffusion area 7, 8.

The air vortex ring F represents a ring-shaped fluid mass, which is formed as described below. When a fluid in a space is compressed and pushed out of the space through a hole, a strong shearing force is generated between the pushed-out fluid and stationary ambient fluid around the hole. Thereby, because the stationary ambient fluid is taken into the pushed-out fluid, the ring-shaped fluid mass can be formed.

Figure 2:
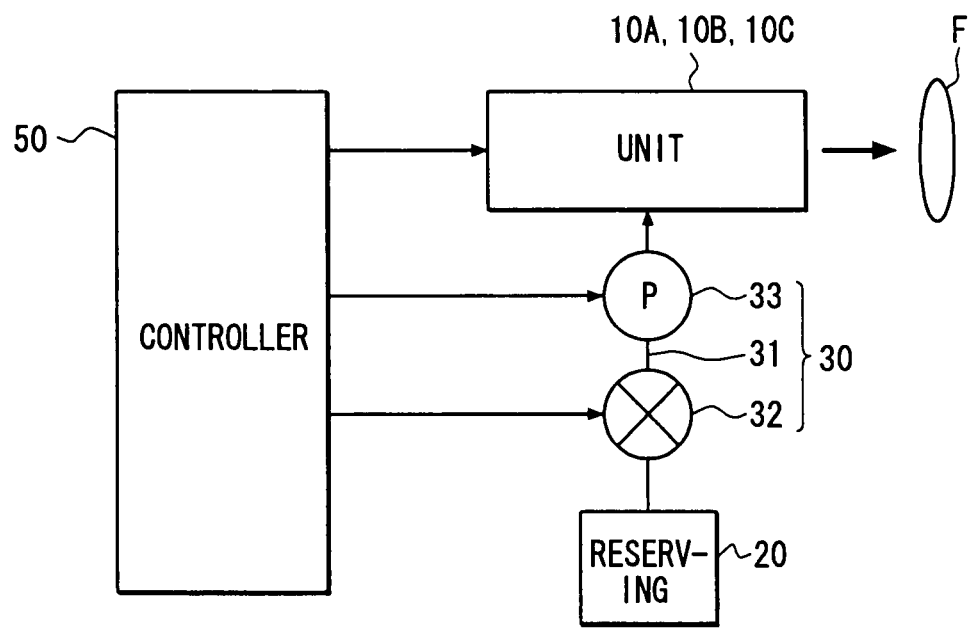
FIG. 2 is a block diagram showing a construction of the device.

As shown in FIG. 2, a conveying portion 30 supplies the gaseous constituent from a reserving portion 20 to the emitting units 10A, 10B, 10C. The reserving portion 20 is constructed with a tank, in which a predetermined gaseous constituent, e.g., moisture or perfume, is stored. The conveying portion 30 includes a connecting tube 31, a valve 32 and a pump 33. The connecting tube 31 connects the reserving portion 20 to a first chamber 130 (to be described below) in the emitting unit 10A, 10B, 10C. The valve 32 opens and closes the connecting tube 31. The pump 33 sends the gaseous constituent from the reserving portion 20 into the first chamber 130.

The valve 32 opens and closes the connecting tube 31 in response to a driving signal output from a controller 50 (to be described below). When the connecting tube 31 is opened by the valve 32, the gaseous constituent flows from the reserving portion 20 into the connecting tube 31. Similarly, the pump 33 operates in response to a driving signal output from the controller 50. The pump 33 sends the gaseous constituent from the connecting tube 31 into the first chamber 130.

Figure 3:
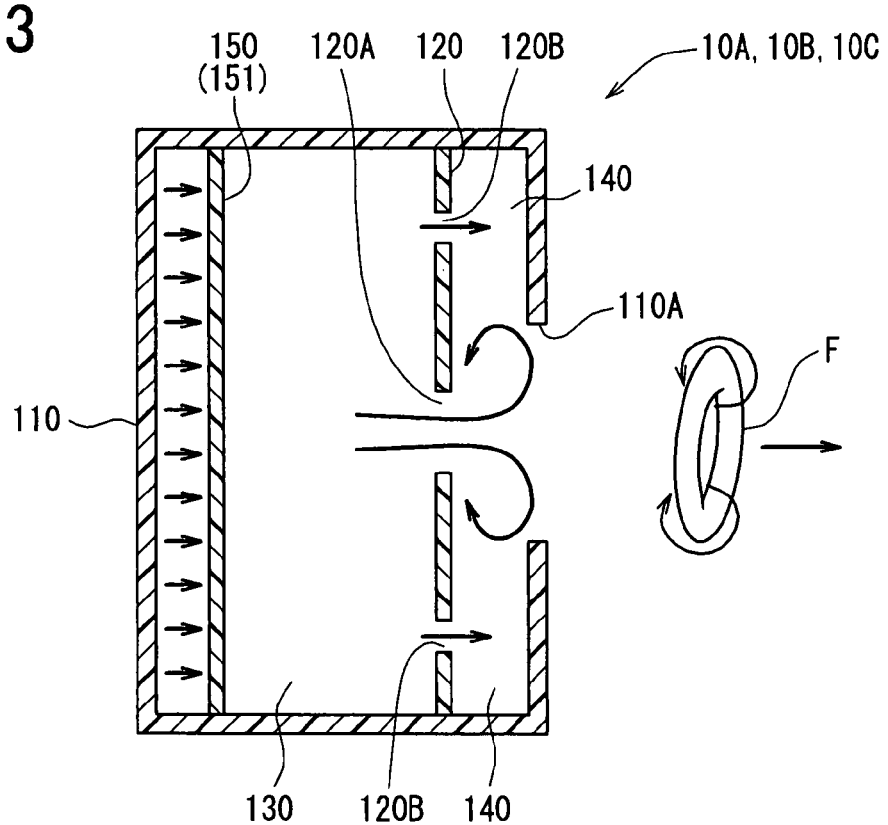
FIG. 3 is a cross-sectional view showing the emitting unit.

The emitting unit 10A, 10B, 10C will be described with reference to FIG. 3. The emitting unit 10A, 10B, 10C includes a case 110, a partition wall 120 and a compressing portion 150. The case 110 has a cylinder shape, and has an air vortex ring emitting outlet 110A in a front face of the case 110. The air vortex ring F is emitted from the case 110 through the emitting outlet 110A. The partition wall 120 divides an inner space of the case 110 into a front space and a rear space. The front space is defined as a second chamber 140 (ring-generating space), in which the air vortex ring F is generated. The rear space is defined as the first chamber 130 for holding the gaseous constituent. The partition wall 120 is disposed closer to the front face (the face having the outlet 110A) of the case 110 than a rear face of the case 110 such that the first chamber 130 is made larger than the second chamber 140.

The partition wall 120 has an opening 120A for making the first chamber 130 and the second chamber 140 to communicate with each other. Specifically, air containing the gaseous constituent in the first chamber 130 is blown into the second chamber 140 though the opening 120A. Each of the opening 120A and the outlet 110A has an approximately round shape, for example, and an axis line of the round shape is approximately the same between the opening 120A and the outlet 110A. An aperture area of the outlet 110A is made larger than that of the opening 120A. Alternatively, a dimension (diameter) of the outlet 110A may be made larger than an external diameter of the emitted air vortex ring F, because the external diameter of the air vortex ring F is usually larger than a dimension (diameter) of the opening 120A.

The partition wall 120 further has plural communication parts 120B in a circumferential direction. The communication part 120B makes the gaseous constituent to flow from the first chamber 130 into the second chamber 140. A sum total (BS) of the aperture areas of the communications parts 120B is made smaller than the aperture area (AS) for the opening 120A. That is, a bypass ratio (i.e., BS/AS) is set equal to or smaller than one.

The first chamber 130 holds the gaseous constituent therein. The first chamber 130 is connected to the reserving portion 20 by the connecting tube 31, and supplied with the gaseous constituent by the valve 32 and the pump 33.

The compressing portion 150 compresses air in the first chamber 130, and is disposed at the rear side of the first chamber 130. The compressing portion 150 includes a board-shaped pressing member 151 movable in the front-and-rear direction. The pressing member 151 is moved in response to a signal output from the controller 50.

The controller 50 controls the valve 32, the pump 33 and the compressing portion 150. For example, a detecting sensor (not shown) for detecting a concentration of the predetermined gaseous constituent is provided in the compartment 2. The controller 50 controls the valve 32, the pump 33 and the compressing portion 150 based on the detected concentration. Specifically, when the detected concentration is equal to or lower than a predetermined value, the controller 50 determines that the gaseous constituent is insufficient in the compartment 2. Then, in order to supply the air vortex ring F to the compartment 2, the valve 32 is opened, and the pump 33 is actuated. Thereafter, the pressing member 151 of the compressing portion 150 is moved to the front side of the case 110.

Next, operation of the device will be described. The controller 50 controls the valve 32, the pump 33 and the compressing portion 150, in order to emit the air vortex ring F. The gaseous constituent is supplied to the first chamber 130 by opening the valve 32 and actuating the pump 33. After the gaseous constituent is supplied to the first chamber 130, the controller 50 sends a control signal to the compressing portion 150, so that the pressing member 151 is moved to the front side, and air in the first chamber 130 is compressed. When the pressing member 151 compresses air in the first chamber 130, a part of the air containing the gaseous constituent in the first chamber 130 is blown into the second chamber 140 through the opening 120A. At the same time, air containing the gaseous constituent is also supplied from the first chamber 130 into the second chamber 140 through the communication part 120B. An amount of air blown into the second chamber 140 through the communication part 120B is smaller than that through the opening 120A.

In the second chamber 140, air blown through the opening 120A is formed into the air vortex ring F. A shearing force is generated between the air blown through the opening 120A and relatively stationary ambient air around the opening 120A. Thereby, the stationary ambient air is also taken into the air blown through the opening 120A. Therefore, the air vortex ring F has a rotating direction shown in FIG. 3.

Because the air blown through the opening 120A entangles the stationary ambient air around the opening 120A, the air blown through the opening 120A sucks in air in the second chamber 140. Therefore, the air vortex ring F is formed by the air blown through the opening 120A and the air in the second chamber 140.

Here, the air blown through the opening 120A contains the gaseous constituent in the first chamber 130. Further, the air in the second chamber 140 also contains the gaseous constituent in the first chamber 130, because the air in the second chamber 140 is blown from the first chamber 130 through the communication part 120B. Therefore, the concentration of the gaseous constituent is approximately the same between the second chamber 140 and the first chamber 130. Thus, the concentration of the gaseous constituent in the air vortex ring F is approximately equal to that in the first chamber 130.

The air vortex ring F is blown into the compartment 2 through the outlet 110A. Here, because the diameter of the outlet 110A is larger than the exterior diameter of the air vortex ring F, the air vortex ring F can be smoothly blown into the compartment 2 without any collision or interference with the case 110.

Figure 4:
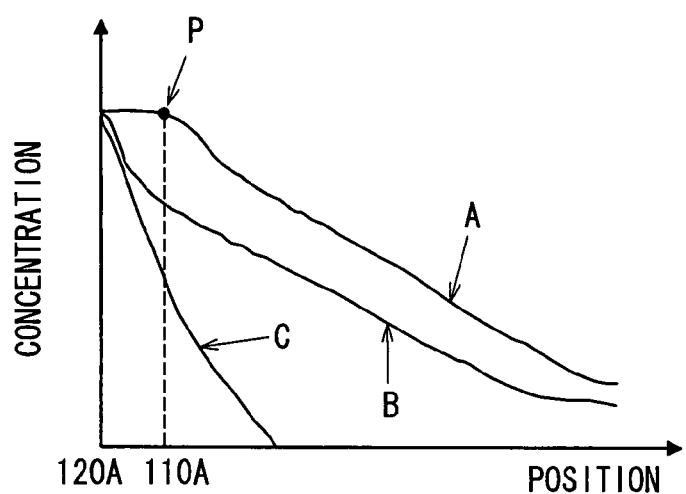
FIG. 4 is a graph showing a relationship between a position of an air vortex ring and a concentration of a gaseous constituent in the vortex ring.

A graph A shown in FIG. 4 shows a relationship between a position of the air vortex ring F in the front-and-rear direction and the concentration of the gaseous constituent in the air vortex ring F. As shown of a point P of the graph A, the concentration of the gaseous constituent at the outlet 110A is approximately equal to that in the first chamber 130. This is because the gaseous constituent is held in the second chamber 140, and because the air vortex ring F is formed in the second chamber 140. In contrast, a graph B shown in FIG. 4 shows the relationship in a comparison example, in which an air vortex ring is formed outside of a case. Because the air vortex ring takes in outside air in the comparison example, the concentration of the gaseous constituent in the air vortex ring is lowered. After the emission of the air vortex ring F, the graph A has a decreasing rate of the concentration of the gaseous constituent, which is approximately equal to that of the graph B, as shown in FIG. 4. Therefore, the air vortex ring F in the first embodiment can keep a high concentration of the gaseous constituent.

In addition, a graph C shown in FIG. 4 shows the relationship in a comparison device, in which only a jet flow from the outlet 110A is blown through an outlet of a case. In this comparison case, the concentration of the gaseous constituent in the jet flow cannot be kept high, because the jet flow is easily diffused. Therefore, the concentration of the gaseous constituent in the jet flow is rapidly decreased, as shown of the graph C in FIG. 4. That is, the gaseous constituent cannot be transmitted to a farther portion in this comparison device, compared with the device in the first embodiment.

According to the first embodiment, the air vortex ring F is formed in the second chamber 140 inside of the case 110, in which the gaseous constituent is held. Therefore, the air vortex ring F can be made of air containing the gaseous constituent. Thus, the concentration of the gaseous constituent in the air vortex ring F can be kept high.

Further, the first chamber 130 and the second chamber 140 are disposed in the same case 110 while being partitioned by the partition wall 120. Therefore, a construction of the device can be made simple, compared with a case where the first chamber 130 and the second chamber 140 are not disposed in the same case 110.

Further, the partition wall 120 has the communication part 120B for making air containing the gaseous constituent to flow from the first chamber 130 into the second chamber 140 outside of the opening 120A. Therefore, the construction of the device can be made much simple, because any supplying portion for supplying the gaseous constituent into the second chamber 140 is not additionally disposed in the second chamber 140.

Further, the sum total of the aperture areas of the communication parts 120B is made smaller than the aperture area of the opening 120A. Therefore, the air vortex ring F can be secured to be formed, because the air vortex ring F made of air blown through the opening 120A is not disrupted by air blown through the communication part 120B.

Further, because the diameter of the outlet 110A is larger than the exterior diameter of the air vortex ring F, the air vortex ring F can be smoothly blown to the compartment 2 without any collision or interference with the case 110.

Second Embodiment

Figure 5A:
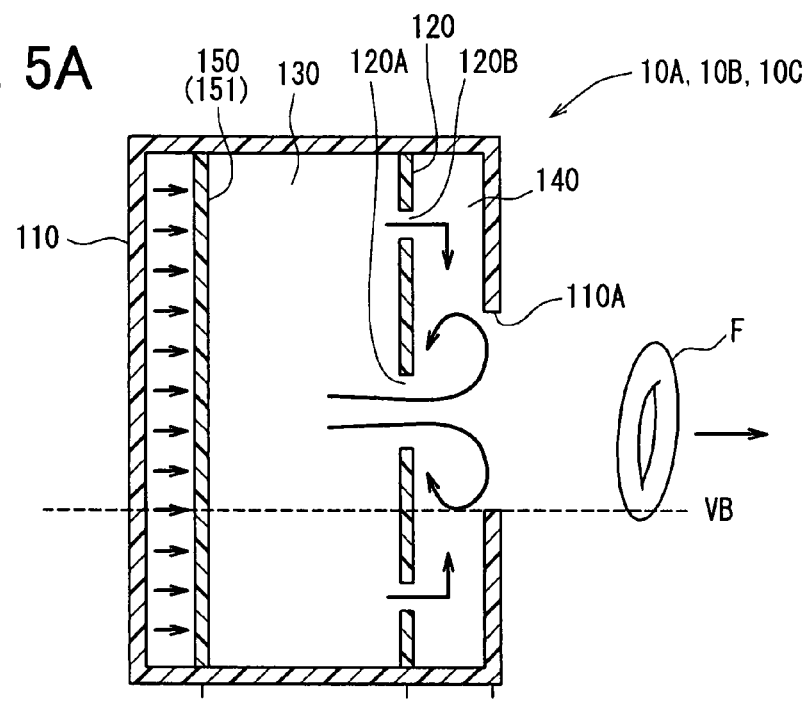
FIG. 5A is a cross-sectional view showing an emitting unit of a gaseous constituent supply device according to a second embodiment.
Figure 5B:
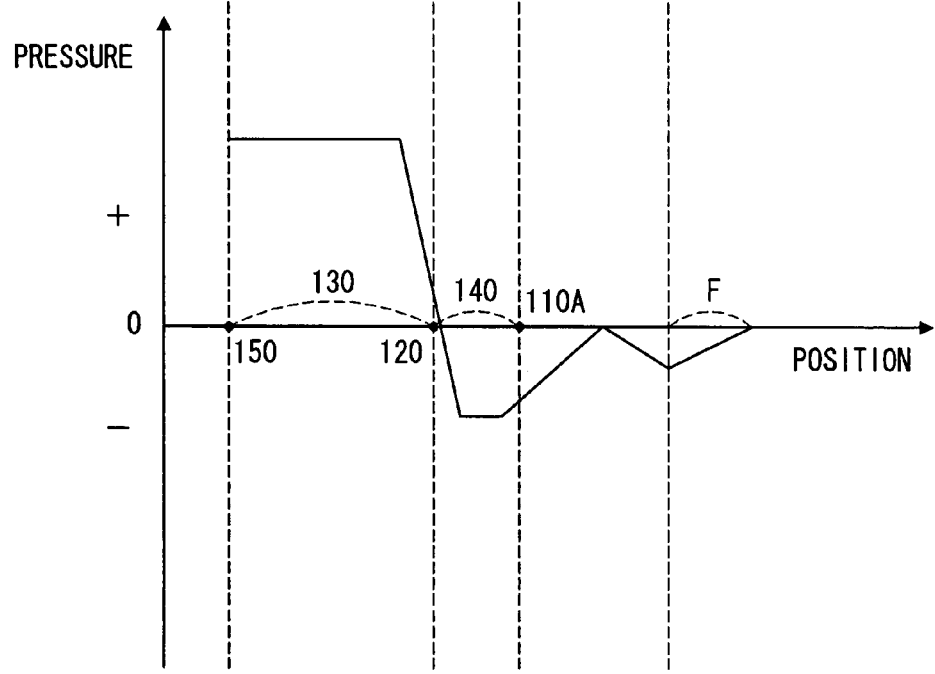
FIG. 5B is a pressure distribution graph showing a relationship between a position on a dashed line VB in FIG. 5A and a pressure.

The second embodiment will be described with reference to FIGS. 5A and 5B. FIG. 5B shows a pressure distribution on a line VB of FIG. 5A. In the second embodiment, an emitting device 10A, 10B, 10C is constructed such that air blown from the first chamber 130 into the second chamber 140 through the opening 120A forms a negative pressure in the second chamber 140. Other parts in the second embodiment may be made similar to the first embodiment. Due to the negative pressure, air in the first chamber 130 is sucked into the second chamber 140 and is formed into an air vortex ring F, when a compressing portion 150 is actuated.

When the compressing portion 150 compresses air in the first chamber 130, a pressure in the first chamber 130 is increased. Further, the negative pressure (minus side pressure in FIG. 5B) is formed around the opening 120A in the second chamber 140, due to air blown through the opening 120A. Therefore, air in the second chamber 140 easily flows toward the opening 120A, due to the negative pressure around the opening 120A. Thereby, a large amount of air in the second chamber 140 can be introduced into the air vortex ring F. Thus, a concentration of a gaseous constituent in the air vortex ring F can be made higher.

Third Embodiment

Figure 6:
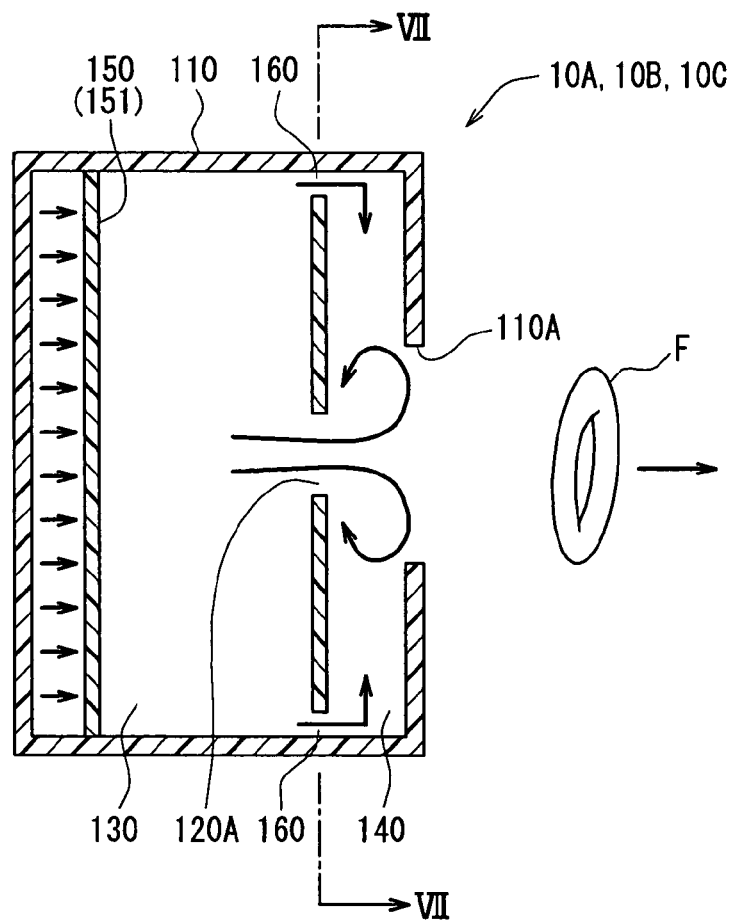
FIG. 6 is a cross-sectional view showing an emitting unit of a gaseous constituent supply device according to a third embodiment.
Figure 7:
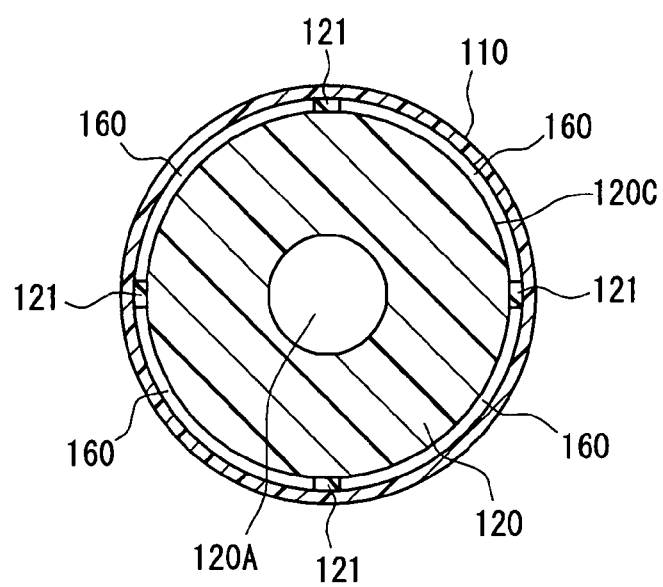
FIG. 7 is a cross-sectional view taken along line VII-VII in FIG. 6.

As shown in FIGS. 6 and 7, a diameter of a partition wall 120 is made smaller than an internal diameter of the case 110, and the partition wall 120 includes four protrusions 121 protruding outside from a circumferential outer end 120C of the partition wall 120 in a diameter direction. The four protrusions 121 are equally spaced from each other in a circumferential direction. The partition wall 120 is fixed to an inner surface of the case 110 by fitting the protrusions 121 on the inner surface of the case 110. Further, a clearance 160 is provided between the inner surface of the case 110 and the circumferential outer end 120C of the partition wall 120. Due to the clearance 160, the first chamber 130 and the second chamber 140 can communicate with each other. That is, the clearance 160 has the same function as the communication part 120B in the above embodiments. Other parts in the third embodiment may be made similar to the above embodiments.

4th Embodiment

Figure 8:
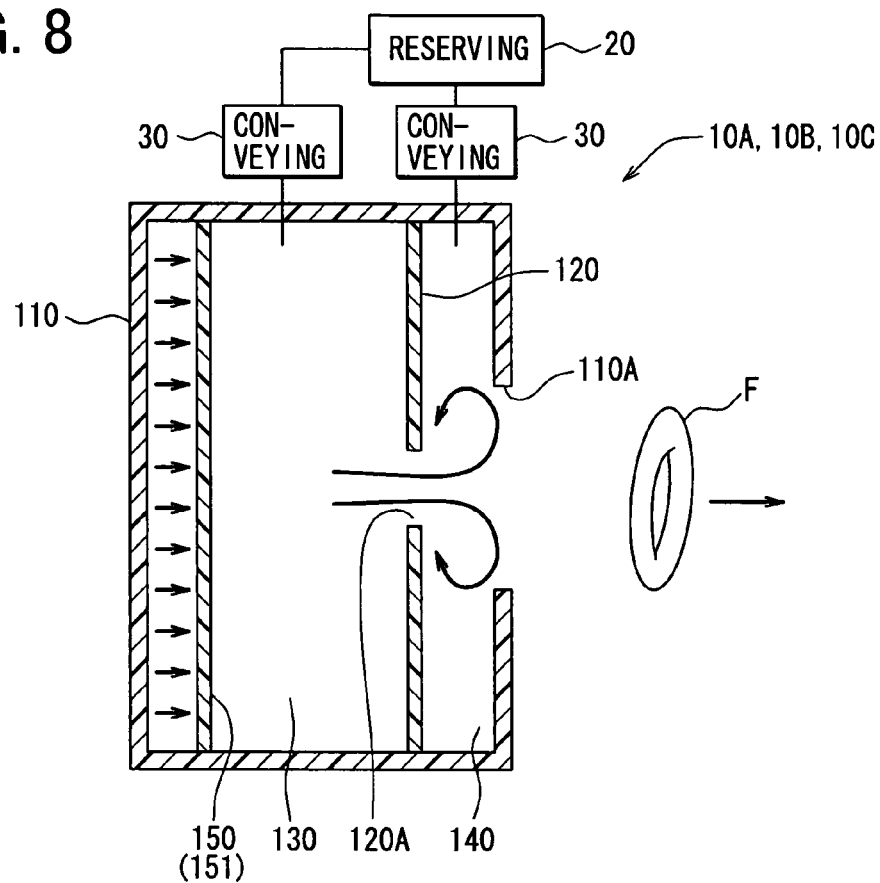
FIG. 8 is a schematic diagram showing an emitting unit of a gaseous constituent supply device according to a 4th embodiment.

As shown in FIG. 8, a conveying portion 30 is also provided for the second chamber 140 so as to directly supply a gaseous constituent from the reserving portion 20 to the second chamber 140. The conveying portion 30 and the reserving portion 20 construct a gaseous constituent supplying portion. A construction of the conveying portion 30 in the 4th embodiment is similar to that in the first embodiment. Further, a communication part 120B is not provided in the partition wall 120 in this embodiment. Other parts in the 4th embodiment may be made similar to the above embodiments.

According to the 4th embodiment, the gaseous constituent can be supplied to the second chamber 140, independently from the first chamber 130.

(Modification)

The communication part 120B is provided in the partition wall 120 in the first and second embodiments. However, the communication part 120B may be eliminated. In this case, the gaseous constituent is directly supplied to the second chamber 140 in advance.

The first chamber 130 and the second chamber 140 are provided in the same case 110 in the above embodiments. Alternatively, the first chamber 130 and the second chamber 140 may be disposed in different cases separately.

The gaseous constituent is supplied to the first chamber 130 and the second chamber 140 by the conveying portions 30 from the single reserving portion 20 in the 4th embodiment. Alternatively, each set of the conveying portion 30 and the reserving portion 20 may be provided to each of the first chamber 130 and the second chamber 140.

5th Embodiment

A 5th embodiment will be described with reference to FIGS. 9 and 10. A gaseous constituent supply device emits an air cannon projectile G containing a predetermined gaseous constituent, and is typically mounted to a vehicle 1. The device is constructed with emitting units 10A, 10B, 10C, which are provided in a compartment 2 of the vehicle 1, in order to supply the gaseous constituent to each occupant 3, 4.

Figure 9:
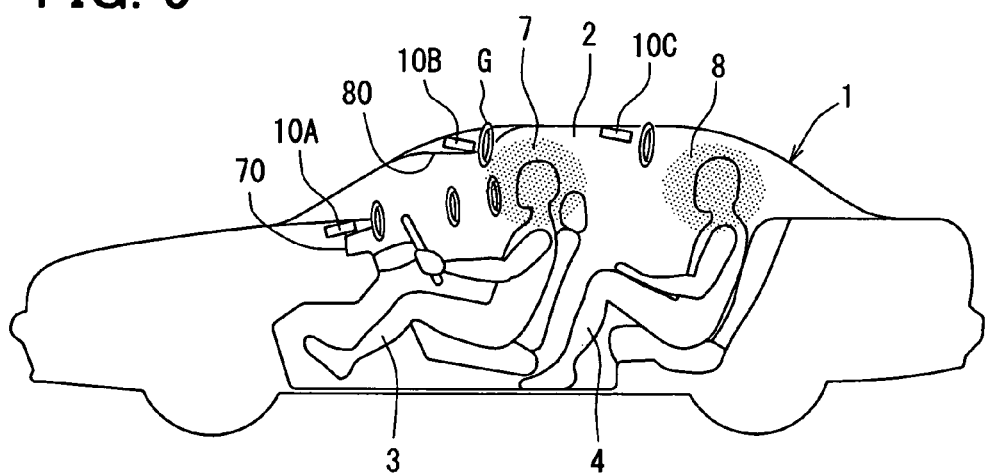
FIG. 9 is a schematic diagram showing an arrangement of emitting units of a gaseous constituent supply device according to a 5th embodiment.
Figure 10:
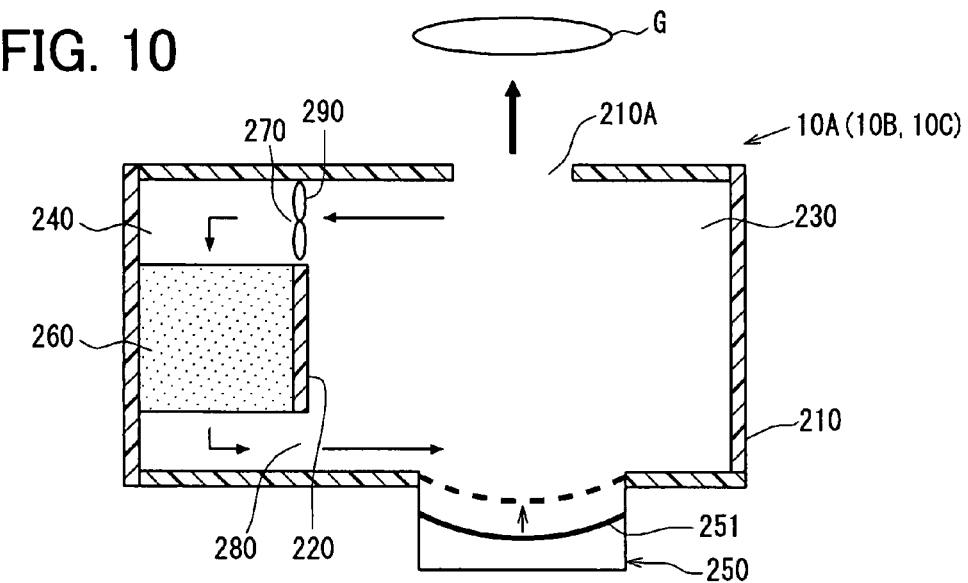
FIG. 10 is a schematic diagram showing the emitting unit of the 5th embodiment.

As shown in FIG. 9, the emitting units 10A, 10B are positioned such that the air cannon projectile G can be emitted toward the occupant 3, and the emitting unit 10C is positioned such that the air cannon projectile G can be emitted toward the occupant 4. Specifically, the emitting unit 10A is disposed in an instrument panel 70, and the emitting unit 10B is disposed in an overhead module 80 on a front seat side ceiling part. The emitting units 10A, 10B emit the air cannon projectiles G toward the occupant 3. In contrast, the emitting unit 10C is disposed on a rear seat side ceiling part, and emits the air cannon projectile G toward the occupant 4.

The air cannon projectile G represents a fluid mass, which is pushed out of a space through an emitting part of the space, after a fluid in the space is compressed. The fluid mass is formed into a vortex ring shape or a sphere shape, for example. When the air cannon projectile G hits a body, e.g., face or shoulder, of the occupant 3, 4, the fluid mass of the air cannon projectile G collapses, and the gaseous constituent contained in the air cannon projectile G diffuses in a diffusion area 7, 8.

The emitting unit 10A, 10B, 10C will be described with reference to FIG. 10. The emitting unit 10A, 10B, 10C includes a case 210, a partition wall 220, a compressing portion 250 and a gaseous constituent generator 260. The partition wall 220 is disposed in the case 210, and divides an inner space of the case 210 into a gaseous constituent chamber 230 and a circulation path 240. The gaseous constituent chamber 230 holds air containing the gaseous constituent. Air in the chamber 230 is circulated through the circulation path 240 in the case 210.

The case 210 has an emitting outlet 210A (emitting part) in a front face of the chamber 230. The emitting outlet 210A is formed into an approximately round shape, and the air cannon projectile G is emitted from the chamber 230 through the emitting outlet 210A. The air cannon projectile G is formed by compressing air in the chamber 230.

The compressing portion 250 for compressing air in the chamber 230 is integrally formed with the case 210. The compressing portion 250 is disposed opposite to the emitting outlet 210A through the chamber 230. The compressing portion 250 includes a membrane-shaped compressing member 251 movable toward the emitting outlet 210 (front side). When the compressing member 251 is moved toward the front side, air in the chamber 230 is compressed.

The gaseous constituent generator 260 is disposed in the circulation path 240, and generates a predetermined gaseous constituent, e.g., perfume or moisture. The generator 260 holds the gaseous constituent in its filter or its case, and the gaseous constituent is in a liquid, solid or gel state in the generator 260.

The partition wall 220 has an intake part 270 (inlet of the circulation path 240) and a discharge part 280 (outlet of the circulation path 240). Air can move from the chamber 230 into the circulation path 240 through the intake part 270, and air can move from the circulation path 240 into the chamber 230 through the discharge part 270. The intake part 270 for taking in air from the chamber 230 into the circulation path 240 is provided at the front side of the partition wall 220, and the discharge part 280 for discharging air from the circulation path 240 into the chamber 230 is provided at the rear side of the partition wall 220.

A fan 290 is disposed adjacent to the intake part 270 of the circulation path 240. A location position of the fan 290 is closer to the intake part 270 than the discharge part 280. Due to the fan 290, air in the chamber 230 can be sent into the circulation path 240.

The partition wall 220, the circulation path 240, the intake part 270, the discharge part 280 and the fan 290 construct a circulating portion. When the fan 290 is actuated, air in the chamber 230 flows into the circulation path 240 through the intake part 270. Then, air flows from the circulation path 240 into the chamber 230 through the discharge part 280. Thus, inner air circulation can be generated in the case 210 by the operation of the fan 290.

Due to the inner air circulation, a concentration of the gaseous constituent in the chamber 230 can be increased. Specifically, when air passes through the circulation path 240, the gaseous constituent generator 260 can supply the gaseous constituent to the air passing through the circulation path 240. Then, the air supplied with the gaseous constituent returns into the chamber 230 again. That is, the concentration of the gaseous constituent in air flowing out of the circulation path 240 is higher than that in air flowing into the circulation path 240.

According to the 5th embodiment, the concentration of the gaseous constituent in the chamber 230 can be increased, because the circulation path 240, the intake part 270, the discharge part 280 and the fan 290 cause the inner air circulation.

Further, the inner space of the case 210 is divided into the chamber 230 and the circulation path 240 through the partition wall 220, and the gaseous constituent generator 260 is disposed in the circulation path 240. Thus, the chamber 230 and the gaseous constituent generator 260 are disposed in the same case 210. Therefore, a construction for circulating air in the case 210 can be simplified, and a size of the device can be reduced.

Further, the fan 290 is used for circulating air in the case 210 between the chamber 230 and the circulation path 240. Therefore, air in the case 210 can be efficiently circulated.

Further, the location position of the fan 290 is closer to the intake part 270 than the discharge part 280. Thus, air in the chamber 230 can easily flow into the circulation path 240. Therefore, the concentration of the gaseous constituent in the chamber 230 can be much increased.

Further, the location position of the emitting outlet 210A is closer to the intake part 270 than the discharge part 280. Thus, when emission of the air cannon projectile G is stopped, the gaseous constituent in the chamber 230 can be restricted from flowing out of the case 210 through the outlet 210A. Therefore, the concentration of the gaseous constituent in the chamber 230 can be kept high.

6th Embodiment

Figure 11:
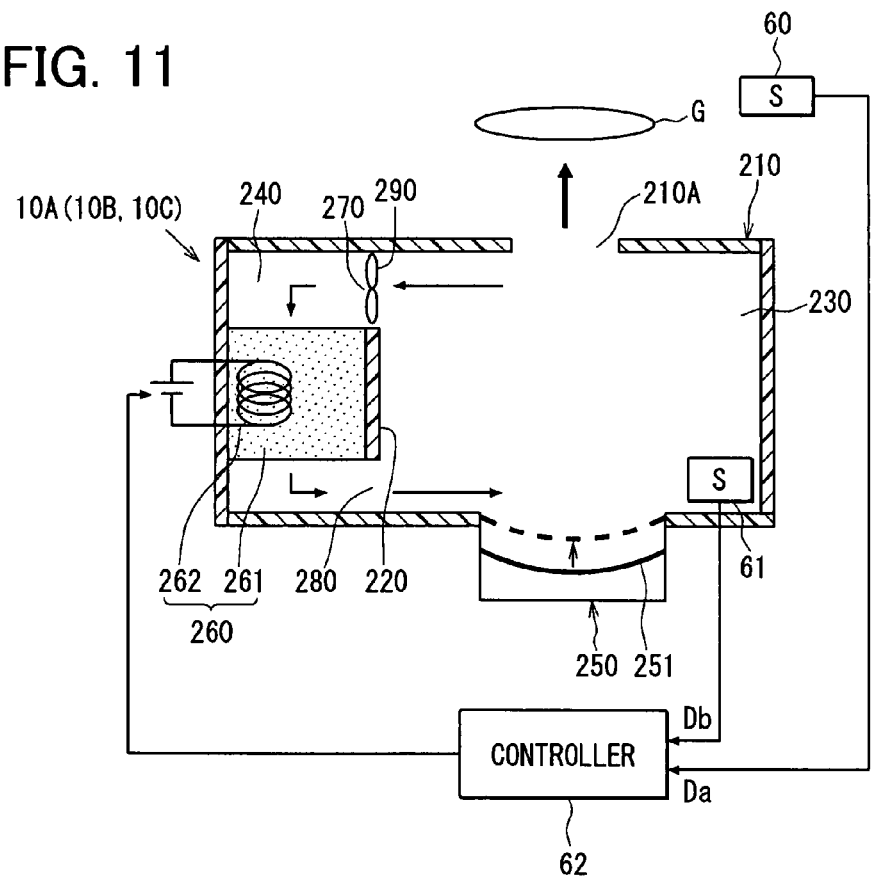
FIG. 11 is a schematic diagram showing an emitting unit of a gaseous constituent supply device according to a 6th embodiment.

As shown in FIG. 11, in a 6th embodiment, a gaseous constituent generator 260 includes a reserving portion 261 for holding a gaseous constituent, and a heater 262 for evaporating the gaseous constituent by heating. A gaseous constituent supply device in the 6th embodiment includes a controller 62 for controlling the heater 262. When the heater 262 is turned on, more gaseous constituent can be generated, because the gaseous constituent is evaporated by the heater 262.

Further, a first detecting sensor 60 is disposed in the compartment 2, and detects a gaseous constituent compartment concentration Da in the compartment 2. For example, the detecting sensor 60 is positioned adjacent to an upper end of a seat back, and detects the concentration of the gaseous constituent adjacent to a face of the occupant 3, 4. In contrast, a second detecting sensor 61 is disposed in the chamber 230, and detects a gaseous constituent chamber concentration Db in the chamber 230.

Figure 12:
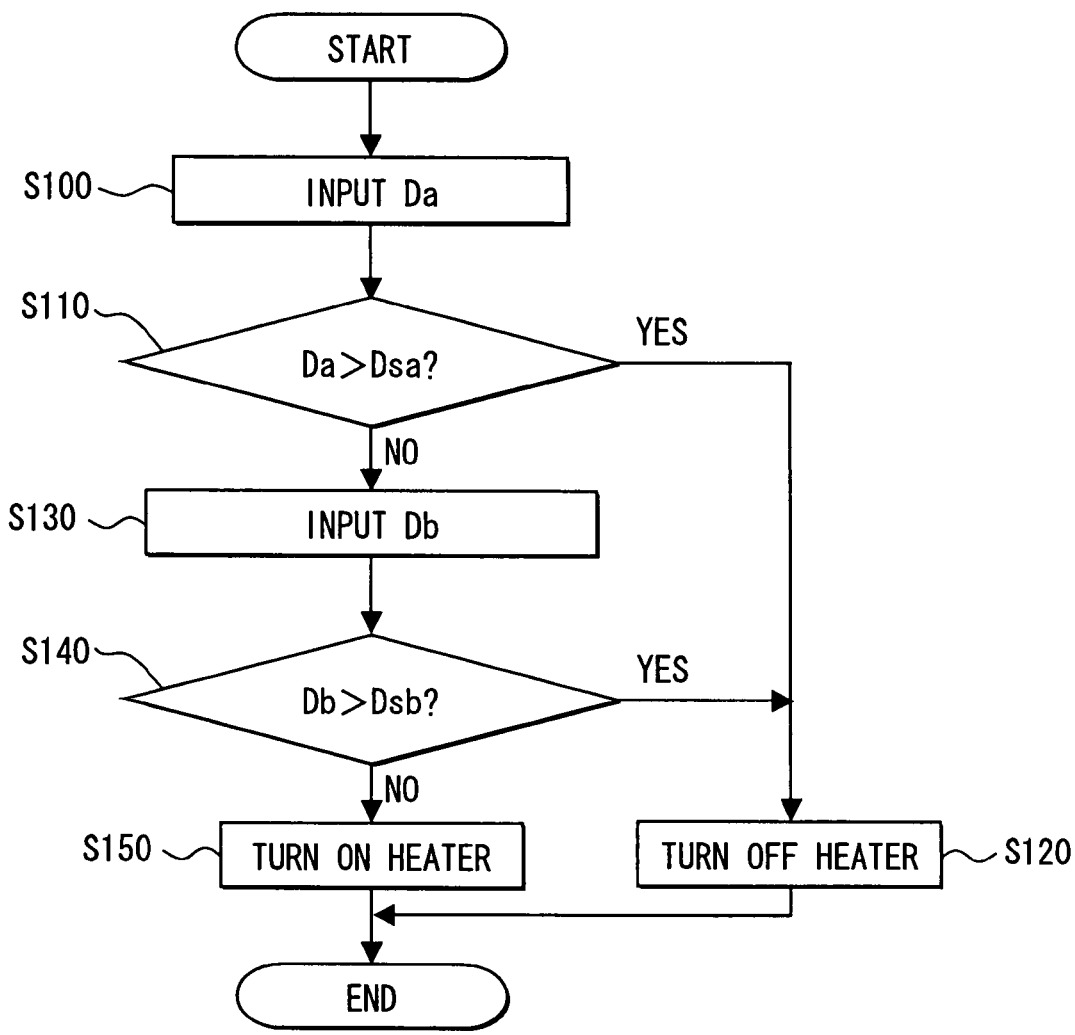
FIG. 12 is a flow chart showing a control of the device of the 6th embodiment.

The controller 62 turns on/off the heater 262 based on the compartment concentration Da detected by the first detecting sensor 60 and the chamber concentration Db detected by the second detecting sensor 61, as shown in FIG. 12.

First, the compartment concentration Da detected by the first detecting sensor 60 is input into the controller 62 (S100), and the compartment concentration Da is compared with a predetermined first value Dsa (S110). When the compartment concentration Da is higher than the first value Dsa (YES at S110), the heater 262 is turned off (S120). In contrast, when the compartment concentration Da is equal to or lower than the first value Dsa (NO at S110), the chamber concentration Db detected by the second detecting sensor 61 is input into the controller 62 (S130).

Then, the chamber concentration Db is compared with a predetermined second value Dsb (S140). The second value Dsb is set in a manner that the air cannon projectile G makes the compartment concentration Da to be equal to the first value Dsa. When the chamber concentration Db is higher than the second value Dsb (YES at S140), the heater 262 is turned off (S120). In contrast, when the chamber concentration Db is equal to or lower than the second value Dsb (NO at S140), the heater 262 is turned on (S150).

That is, when the compartment concentration Da is higher than the first value Dsa, or when the chamber concentration Db is higher than the second value Dsb, the heater 262 is turned off. Thereby, the chamber concentration Db can be lowered, because an amount of the gaseous constituent generated by the generator 260 can be reduced. Therefore, the compartment concentration Da is made closer to the first value Dsa.

In contrast, when the compartment concentration Da is equal to or lower than the first value Dsa, and when the chamber concentration Db is equal to or lower than the second value Dsb, the heater 262 is turned on. Thereby, the chamber concentration Db can be increased, because an amount of the gaseous constituent generated by the generator 260 can be increased. Therefore, the compartment concentration Da can be made to be approached to the first concentration Dsa, because the amount of the gaseous constituent contained in the air cannon projectile G can be increased.

According to the 6th embodiment, the heater 262 is turned on/off so as to make the compartment concentration Da to be approached to the first value Dsa. Thus, the concentration of the gaseous constituent in the compartment 2 can be kept appropriate.

7th Embodiment

Figure 13:
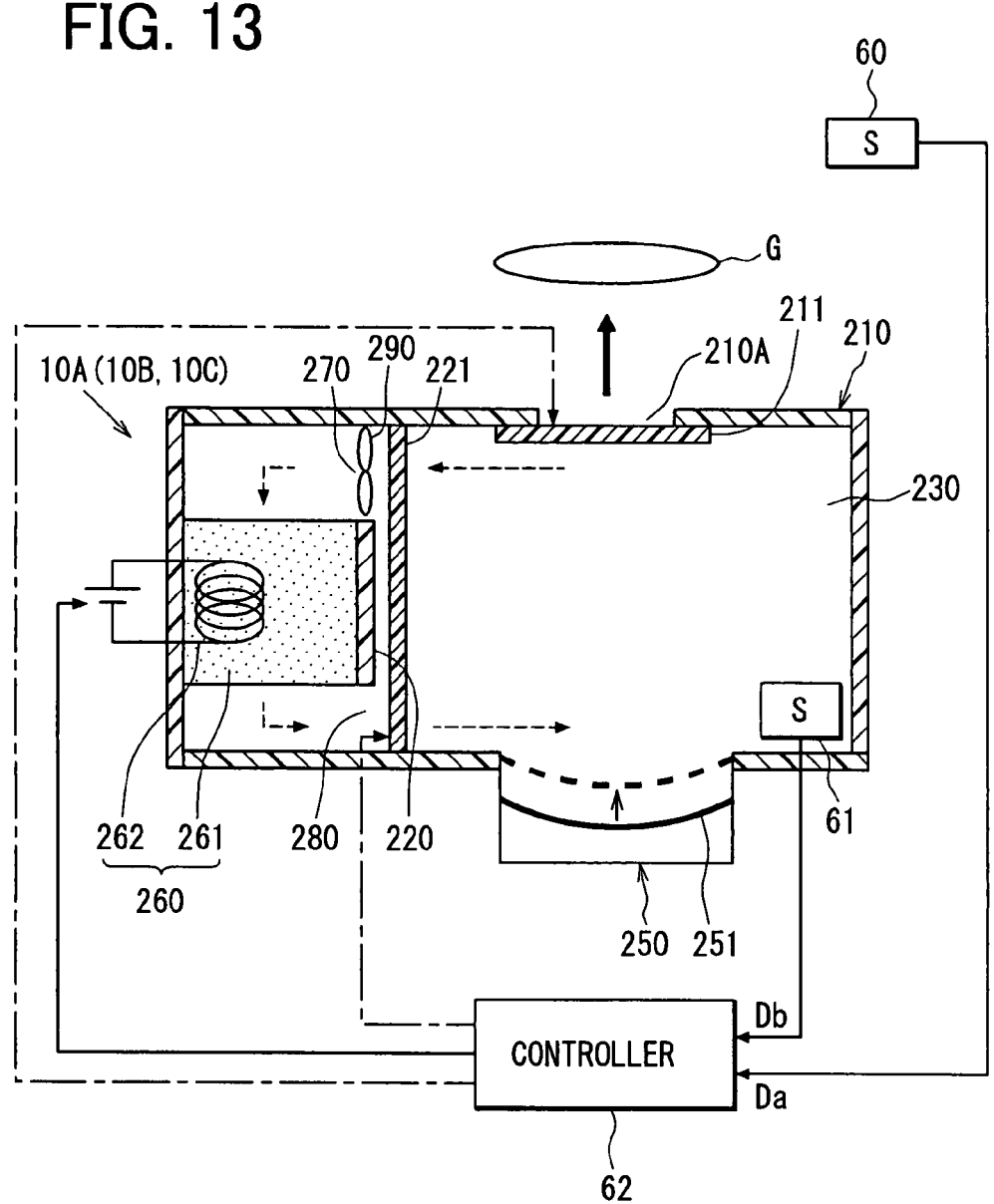
FIG. 13 is a schematic diagram showing an emitting unit of a gaseous constituent supply device according to a 7th embodiment.

As shown in FIG. 13, a gaseous constituent supply unit 10A, 10B, 10C in a 7th embodiment includes a first shutter 211 for opening and closing the emitting outlet 210A, and a second shutter 221 for opening and closing the intake part 270 and the discharge part 280. Ordinarily, the outlet 210A, the intake part 270 and the discharge part 280 are open. When a control signal is output from the controller 62 to the first shutter 211, the first shutter 211 closes the outlet 210A. When a control signal is output from the controller 62 to the second shutter 211, the second shutter 211 closes the intake part 270 and the discharge part 280.

Figure 14:
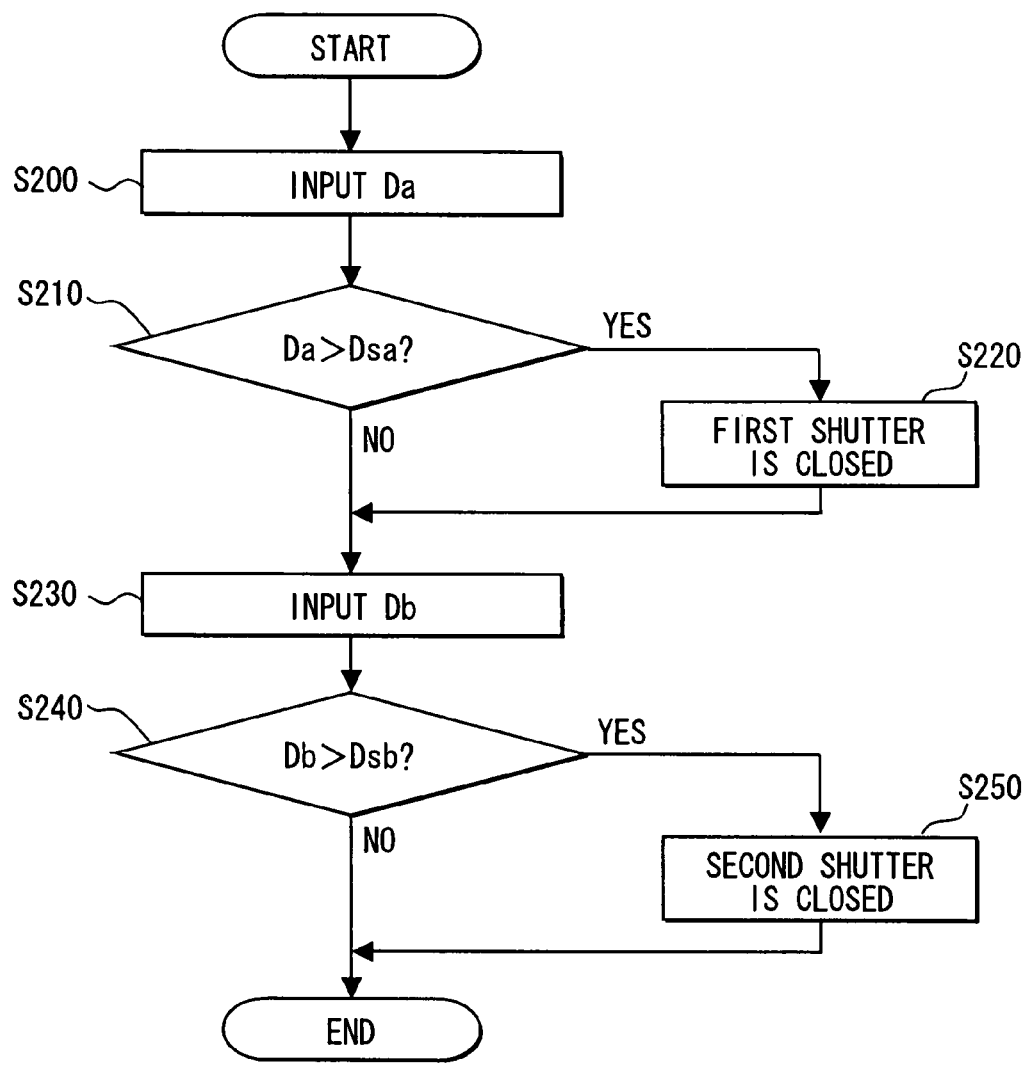
FIG. 14 is a flow chart showing a control of the device of the 7th embodiment.

The controller 62 outputs the signal to the shutter 211, 221 based on the compartment concentration Da detected by the first sensor 60 and the chamber concentration Db detected by the second sensor 61, as shown in FIG. 14.

First, the compartment concentration Da detected by the first sensor 60 is input into the controller 62 (S200), and the detected compartment concentration Da is compared with a predetermined first value Dsa (S210). When the compartment concentration Da is higher than the first value Dsa (YES at S210), the first shutter 211 closes the outlet 210A (S220). In contrast, when the compartment concentration Da is equal to or lower than the first value Dsa (NO at S210), the chamber concentration Db is detected by the second sensor 61 and is input into the controller 62 (S230).

Then, the chamber concentration Db is compared with a predetermined second value Dsb (S240). When the chamber concentration Db is higher than the second value Dsb (YES at S240), the second shutter 221 closes the intake part 270 and the discharge part 280 (S250).

When the compartment concentration Da is equal to or lower than the first value Dsa (NO at S210), the first shutter 211 is kept to be open. Further, when the chamber concentration Db is equal to or lower than the second value Dsb (NO at S240), the first and second shutters 211, 221 are kept to be open.

That is, when the compartment concentration Da is equal to or lower than the first value Dsa, the first shutter 211 is open so as to emit the air cannon projectile G containing the gaseous constituent to the compartment 2. In contrast, when the compartment concentration Da is higher than the first value Dsa, the first shutter 211 is actuated to close the outlet 210A. Thus, the compartment concentration Da can be adjusted and can be restricted from being too much higher. Therefore, the compartment concentration Da can be kept appropriate.

In contrast, when the chamber concentration Db is equal to or lower than the second value Dsb, the second shutter 221 is open so as to supply the gaseous constituent to the chamber 230. In contrast, when the chamber concentration Db is higher than the second value Dsb, the second shutter 221 is actuated to close the intake part 270 and the discharge part 280. Thus, the chamber concentration Db can be made closer to the second value Dsb. Therefore, the concentration of the gaseous constituent in the compartment 2 can be kept appropriate, because the air cannon projectile G can have an appropriate concentration of the gaseous constituent.

(Modification)

The fan 290 is positioned closer to the intake part 270 than the discharge part 280 in the 5th, 6th and 7th embodiments. However, the fan 290 may be positioned closer to the discharge part 280 than the intake part 270.

The outlet 210A is positioned closer to the intake part 270 than the discharge part 280 in the 5th, 6th and 7th embodiments. However, the outlet 210A may be positioned closer to the discharge part 280 than the intake part 270.

Both of the compartment concentration Da and the chamber concentration Db are detected, and the heater 262 is controlled based on both of the compartment concentration Da and the chamber concentration Db in the 6th and 7th embodiments. However, the heater 262 may be controlled based on at least one of the compartment concentration Da and the chamber concentration Db.

The controller 62 controls the heater 262 by an on/off control in the 6th embodiment. However, heating operation of the heater 262 may be gradually continuously controlled based on a difference between the compartment concentration Da and the first value Dsa, or a difference between the chamber concentration Db and the second value Dsb.

Both of the first and second shutters 211, 221 are provided in the 7th embodiment. However, only one of the shutters 211, 221 may be provided.

The second shutter 221 opens and closes both of the intake part 270 and the discharge part 280. However, different shutters may be provided to each of the intake part 270 and the discharge part 280 separately. Further, the second shutter 221 may open and close only one of the intake part 270 and the discharge part 280.

8th Embodiment

An 8th embodiment will be described with reference to FIGS. 15-18. A gaseous constituent supply device emits an air cannon projectile G containing a predetermined gaseous constituent, and is typically mounted to a vehicle 1. The device is constructed with emitting units 10A, 10B, 10C, which are provided in a compartment 2 of the vehicle 1, in order to supply the gaseous constituent to each occupant 3, 4.

Figure 15:
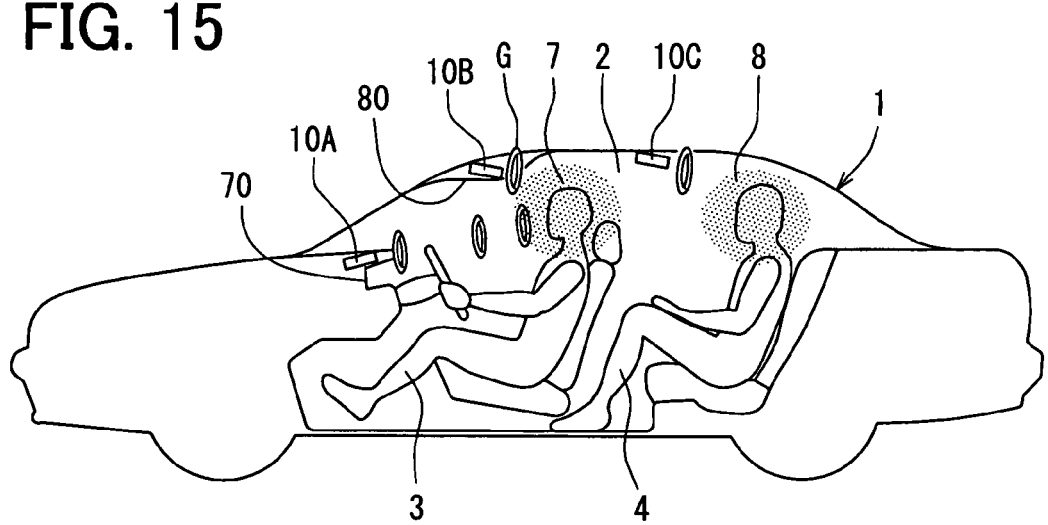
FIG. 15 is a schematic diagram showing an arrangement of emitting units of a gaseous constituent supply device according to an 8th embodiment.

As shown in FIG. 15, the emitting units 10A, 10B are positioned such that the air cannon projectile G can be emitted toward the occupant 3, and the emitting unit 10C is positioned such that the air cannon projectile G can be emitted toward the occupant 4. Specifically, the emitting unit 10A is disposed in an instrument panel 70, and the emitting unit 10B is disposed in an overhead module 80 on a front seat side ceiling part. The emitting units 10A, 10B emit the air cannon projectile G toward the occupant 3. In contrast, the emitting unit 10C is disposed on a rear seat side ceiling part, and emits the air cannon projectile G toward the occupant 4.

The air cannon projectile G represents a fluid mass, which is pushed out of a space through an emitting outlet of the space, after a fluid in the space is compressed. The fluid mass is formed into a vortex ring shape or a sphere shape, for example. When the air cannon projectile G hits a body, e.g., face or shoulder, of the occupant 3, 4, the fluid mass of the air cannon projectile G collapses, and the gaseous constituent contained in the air cannon projectile G diffuses in a diffusion area 7, 8.

Figure 16:
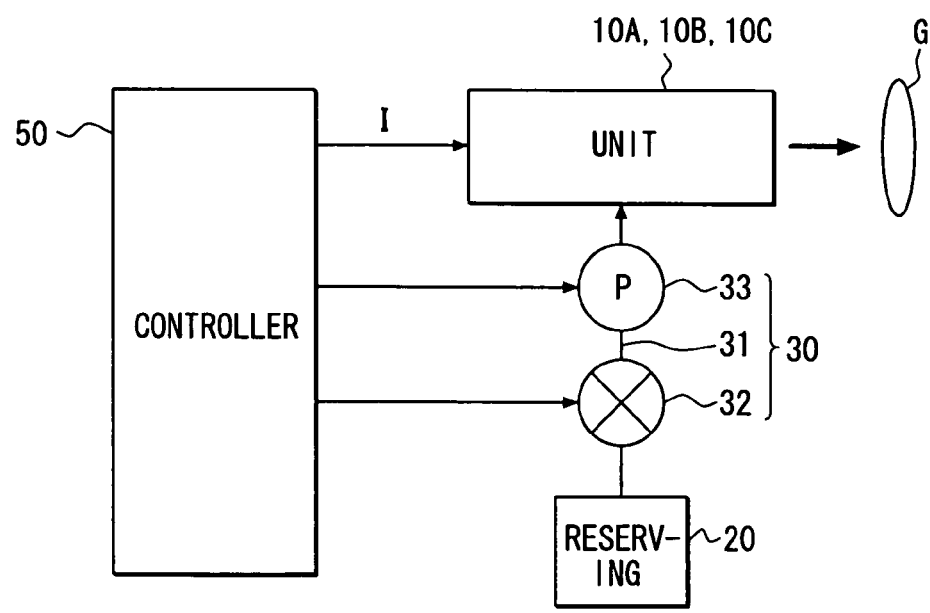
FIG. 16 is a block diagram showing a construction of the device of the 8th embodiment.

As shown in FIG. 16, a conveying portion 30 supplies the gaseous constituent stored in a reserving portion 20 to the emitting units 10A, 10B, 10C. The reserving portion 20 is constructed with a tank, in which a predetermined gaseous constituent, e.g., moisture or perfume, is stored. The conveying portion 30 includes a connecting tube 31, a valve 32 and a pump 33. The connecting tube 31 connects the reserving portion 20 to a gaseous constituent chamber 320 (to be described below) in the emitting unit 10A, 10B, 10C. The valve 32 opens and closes the connecting tube 31. The pump 33 sends the gaseous constituent from the reserving portion 20 into the chamber 320.

The valve 32 opens and closes the connecting tube 31 in response to a driving signal output from a controller 50 (to be described below). When the valve 32 opens the connecting tube 31, the gaseous constituent flows from the reserving portion 20 into the connecting tube 31. Similarly, the pump 33 operates in response to a driving signal output from the controller 50. The pump 33 sends the gaseous constituent from the connecting tube 31 into the chamber 320.

Figure 17:
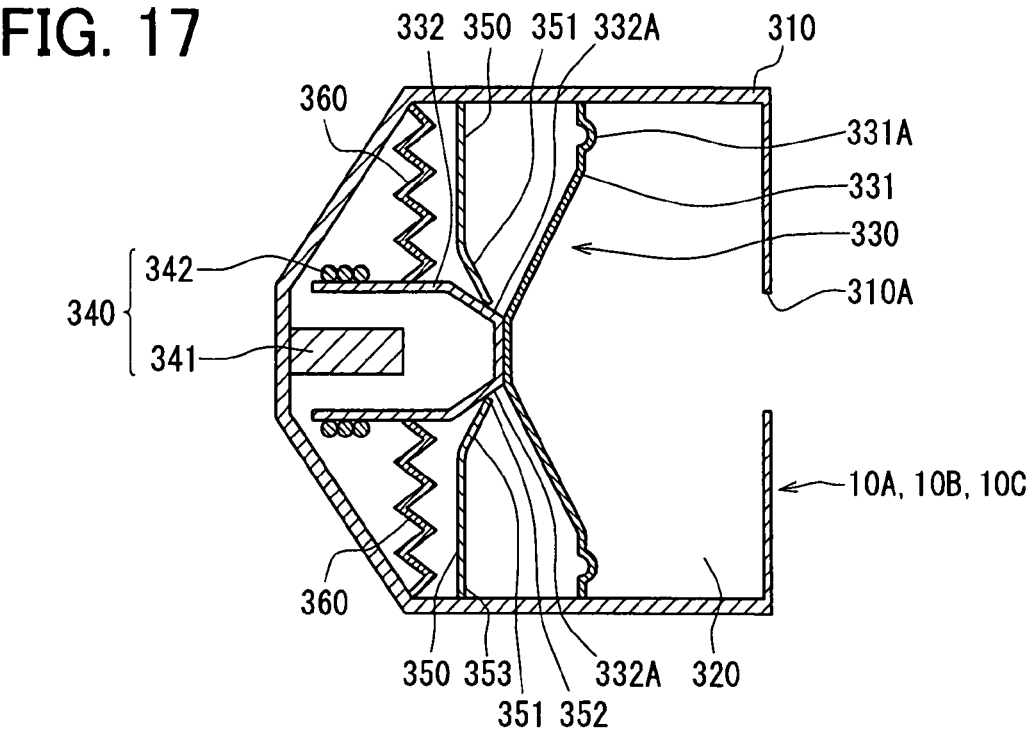
FIG. 17 is a cross-sectional view showing the emitting unit in which a compressive member is positioned at a reference position of the 8th embodiment.

As shown in FIG. 17, the emitting unit 10A, 10B, 10C includes the chamber 320, a compressing portion 330, a driving portion 340, a damper 350 (restricting portion) and a supporting portion 360 in a case 310. The chamber 320 holds the gaseous constituent therein. The compressing portion 330 compresses air in the chamber 320. The driving portion 340 drives the compressing portion 330. The damper 350 restricts a displacement of the compressing portion 330. The supporting portion 360 supports a pressing member 332 of the compressing portion 330.

The case 310 has approximately a cylinder shape, for example, and has an air cannon projectile emitting outlet 310A in a front face of the case 310. The outlet 310A has an approximately round shape, for example. The air cannon projectile G is emitted from the case 310 through the emitting outlet 310A into the compartment 2. The chamber 320 is connected to the reserving portion 20 by the connecting tube 31, and supplied with the gaseous constituent by the valve 32 and the pump 33. Thus, the chamber 320 holds air containing the gaseous constituent therein.

The compressing portion 330 is positioned to be opposite to the emitting outlet 310A. The compressing portion 330 includes a compressive member 331 displaceable toward the emitting outlet 310A (front side), and the pressing member 332 for pressing the compressive member 331.

Figure 18:
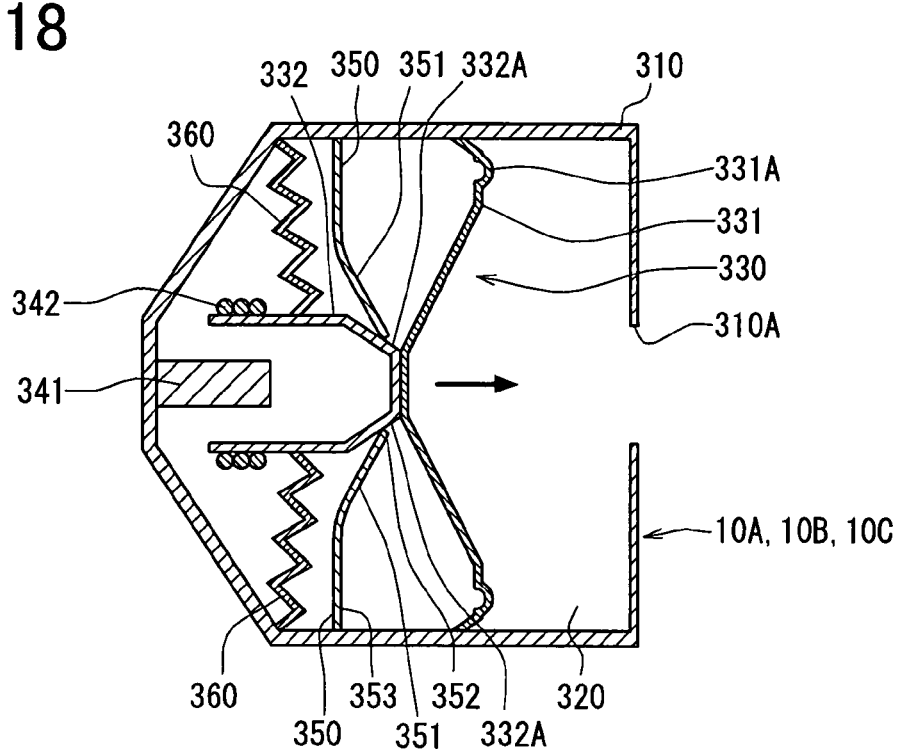
FIG. 18 is a cross-sectional view showing the emitting unit in which the compressive member is positioned at a compression position of the 8th embodiment.

The compressive member 331 has an approximately round shape, and a periphery of the compressive member 331 is fixed to the case 310. Because the periphery of the compressive member 331 has an edge portion 331A, the compressive member 331 is displaceable in a front-and-rear direction. The compressive member 331 shown in FIG. 17 is in a reference position, in which the compressive member 331 is spaced from the emitting outlet 310A by a predetermined dimension. At this time, the damper 350 is not deformed. Then, the compressive member 331 can be displaced toward the emitting outlet 310A so as to compress air in the chamber 320, as shown in FIG. 18. At this time, the compressive member 331 is in a compression position. Thereby, the air cannon projectile G containing the gaseous constituent can be emitted to the compartment 2 through the emitting outlet 310A.

The pressing member 332 has approximately a cylinder shape, for example, and has a taper 332A tapering toward the compressive member 331. An end of the taper 332A is integrated with the compressive member 331. A coil 342 of the driving portion 340 is twisted around a base of the pressing member 332.

The driving portion 340 includes a pair of a magnet 341 and the coil 342. The magnet 341 is fixed to an inner rear face of the case 310, and the coil 342 is integrated with the pressing member 332. The magnet 341 has a cylinder shape, and protrudes from the inner rear face of the case 310 toward the front side. The magnet 341 is positioned at a rear side in an inner space of the pressing member 332. Because the coil 342 is twisted around the base of the pressing member 332, the coil 342 is positioned to surround the magnet 341. The coil 342 of the emitting unit 10A, 10B, 10C is supplied with a driving current I from the controller 50, as shown in FIG. 16.

When the controller 50 supplies the driving current I to the coil 342, the magnet 341 generates a magnetic field. Then, the magnetic field generates a Lorentz force. Due to the Lorentz force, the coil 342 has a bias force toward the front side. Thereby, the pressing member 332 integrated with the coil 342 can press the compressive member 331. Thus, the compressive member 331 can be displaced toward the emitting outlet 310A from the reference position. In contrast, when the controller 50 stops the supply of the driving current I, the compressive member 331 returns to the reference position, because the bias force is not generated.

The driving current I is applied with a predetermined wave necessary for generating the air cannon projectile G. For example, the driving current I is a rectangular-wave current. Because a power of the Lorentz force is determined based on amplitude of the rectangular-wave of the current I, a displacement dimension of the compressive member 331 can be determined based on the amplitude of the rectangular-wave of the current I.

The damper 350 has a membrane shape, and is made of a flexible material having a self-returning force, e.g., rubber or urethane. The damper 350 has a protrusion 351 at its approximately center part. The protrusion 351 has a trapezoid shape tilting and protruding toward the front side. The protrusion 351 has an aperture in its approximately center part. A shape of the aperture of the protrusion 351 is approximately similar to a cross-sectional shape of the taper 332A. The pressing member 332 is arranged in the aperture of the protrusion 351 by being inserted from the rear side. An inner circumferential end 352 of the damper 350 is in contact with the taper 332A of the pressing member 332, and an outer circumferential end 353 of the damper 350 is fixed to the inner surface of the case 310. That is, the inner end 352 of the damper 350 is displaceable in the front-and-rear direction together with the pressing member 332, and the outer end 353 of the damper 350 is not displaceable.

The supporting portion 360 supports the pressing member 332, and is formed by folding a membrane material into a wave shape. The supporting portion 360 has a ring shape, corresponding to the shapes of the case 310 and the pressing member 332. An outer end of the supporting portion 360 is fixed to the inner surface of the case 310, and an inner end of the supporting portion 360 is fixed to the pressing member 332. The supporting portion 360 can support the pressing member 332, even when the pressing member 332 is moved, because the supporting portion 360 has the wave shape and can be elastically deformed. When the pressing member 332 is displaced, the inner end of the supporting portion 360 can be displaced with the pressing member 332.

Here, the controller 50 controls the valve 32, the pump 33 and the driving current I, as shown in FIG. 16. For example, a detecting sensor for detecting a concentration of the gaseous constituent is disposed in the compartment 2, and the controller 50 controls the valve 32, the pump 33 and the driving current I based on the detected concentration of the gaseous constituent in the compartment 2. Specifically, when the concentration of the gaseous constituent is equal to or lower than a predetermined value, the controller 50 opens the valve 32, actuates the pump 33 and supplies the driving current I to the coil 342 so as to emit the air cannon projectile G to the compartment, because the gaseous constituent is determined to be insufficient in the compartment 2.

Next, operation of the device will be described. The controller 50 controls the valve 32, the pump 33 and the driving current I, so as to timely emit the air cannon projectile G. That is, the controller 50 opens the valve 31 and actuates the pump 33 so as to supply the gaseous constituent to the chamber 320, and the controller 50 supplies the driving current I to the coil 342 such that the pressing member 332 presses the compressive member 331 toward the front side. Thereby, the compressive member 331 is displaced from the reference position to the front side, and air in the chamber 320 is compressed. Thus, the air cannon projectile G containing the gaseous constituent is emitted toward the occupant 3, 4 through the emitting outlet 310A.

When the compressive member 331 is displaced from the reference position to the compression position (from FIG. 17 to FIG. 18), the inner end 352 of the damper 350 is displaced toward the front side. Therefore, the damper 350 is deformed. A deformation dimension of the damper 350 is increased, when the displacement dimension of the compressive member 331 is increased. At the same time, the self-returning force (elastic force) of the damper 350 toward the reference position is increased. That is, the self-returning force of the damper 350 toward the reference position is increased, when the displacement dimension of the compressive member 331 is increased. Thus, the damper 350 has a restricting force restricting the compressive member 331 toward the reference position, and the restricting force is increased.

The compressive member 331 is displaced toward a target position, e.g., the compression position, while the damper 350 restricts the displacement of the compressive member 331. Therefore, the compressive member 331 does not vibrate around the target position, because the damper 350 restricts the displacement of the compressive member 331, even immediately after a rising of the driving current I.

According to the 8th embodiment, when the compressive member 331 is displaced toward the front side, the damper 350 has the restricting force relative to the compressive member 331 toward the reference position. Therefore, the compressive member 331 does not vibrate around the target position. That is, noise can be reduced, because a transient distortion is reduced. Further, because the damper 350 has the restricting force relative to the compressive member 331 in accordance with the displacement dimension of the compressive member 331, the transient distortion can be reduced, even when the displacement dimension of the compressive member 331 is increased. Furthermore, because the damper 350 is made of an elastic material, e.g., rubber or urethane, the damper 350 has a suitable elastic force relative to the compressive member 331 in accordance with the displacement dimension of the compressive member 331. Thus, the transient distortion can be efficiently reduced.

Figure 19:
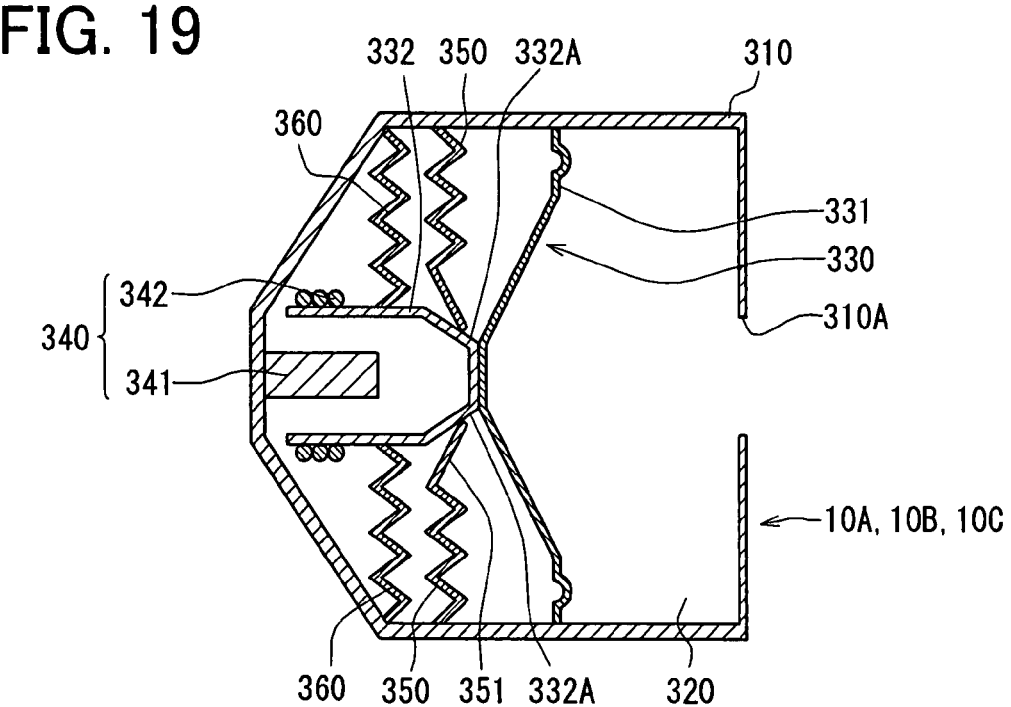
FIG. 19 is a cross-sectional view showing a modification of the emitting unit of the 8th embodiment.

However, the damper 350 may not be made of the elastic material. In this case, as shown in FIG. 19, the damper 350 except for the protrusion 351 is formed into a wave shape. Thereby, the transient distortion can be efficiently reduced, because the damper 350 has the restricting force in accordance with the displacement dimension of the compressive member 331.

Figure 20:
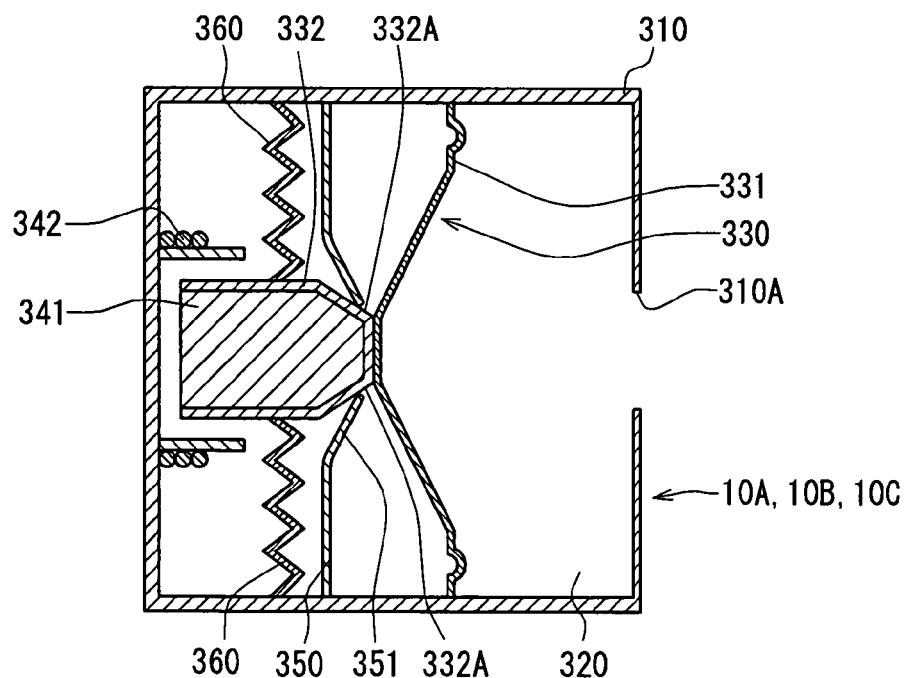
FIG. 20 is a cross-sectional view showing another modification of the emitting unit.

As shown in FIG. 20, the coil 342 may be fixed to a protrusion of the case 310, and the magnet 341 may be integrated with the pressing member 332. In this case, the pressing member 332 integrated with the magnet 341 can be biased toward the front side, due to the Lorentz force. Thus, the compressive member 331 can be displaced toward the front side.

9th Embodiment

Figure 21:
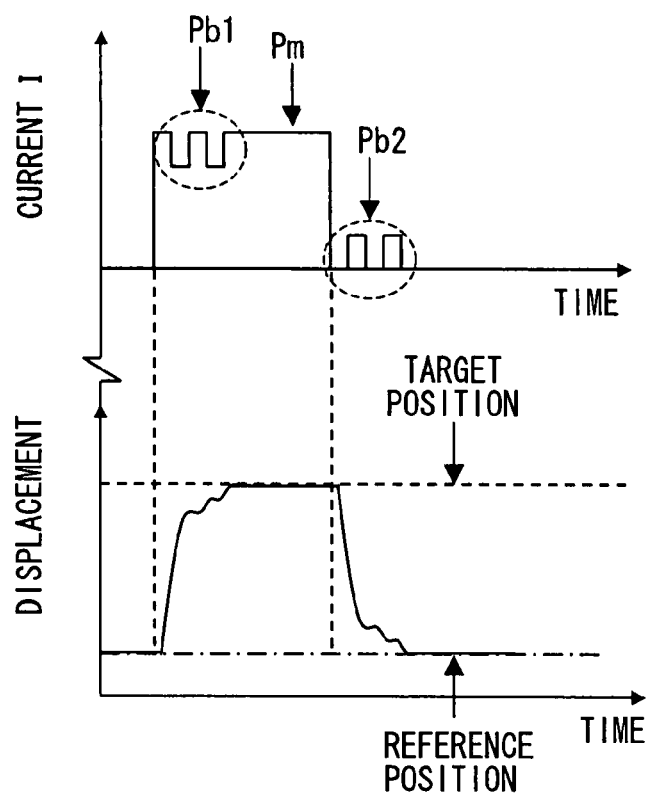
FIG. 21 is a graph showing a relationship between a time and a current, and a displacement of a compressive member of a gaseous constituent supply device according to a 9th embodiment.

The damper 350 is eliminated in a 9th embodiment. As shown in FIG. 21, a main pulse Pm overlapped with a brake pulse Pb (Pb1, Pb2) is supplied to the coil 342, as the driving current I. The main pulse Pm is used for emitting an air cannon projectile G, and the brake pulse Pb is used for reducing vibrations of the compressive member 331. The vibrations are caused by the transient distortion, when the main pulse Pm is supplied to the coil 342.

The brake pulse Pb includes a negative pulse Pb1 and a positive pulse Pb2. The negative pulse Pb1 is overlapped with the main pulse Pm, after a rising of the main pulse Pm. The positive pulse Pb2 is overlapped with the main pulse Pm, after a falling of the main pulse Pm. Each amplitude of the brake pulses Pb1, Pb2 is determined based on amplitude of the main pulse Pm. Therefore, the vibrations of the compressive member 331 caused by the transient distortion can be reduced. Each pulse-number of the brake pulses Pb1, Pb2 is determined such that the vibrations of the compressive member 331 caused by the transient distortion can be effectively reduced. Pulse-period is approximately the same between the brake pulses Pb1, Pb2.

The driving current I including the main pulse Pm and the brake pulse Pb is supplied to the coil 342. Due to the brake pulse Pb1, the displacement of the compressive member 331 does not overpass a target position at the rising of the main pulse Pm, as shown in FIG. 21. Therefore, the vibrations of the compressive member 331 can be reduced, because the brake pulse Pb1 restricts the displacement of the compressive member 331 toward the target position. Similarly, at the falling of the main pulse Pm, the vibrations of the compressive member 331 can be reduced, because the brake pulse Pb2 restricts the displacement of the compressive member 331 toward the reference position.

According to the 9th embodiment, the vibrations of the compressive member 331 can be reduced, because the brake pulses Pb1, Pb2 restrict the displacement of the compressive member 331. Further, when each amplitude of the brake pulses Pb1, Pb2 is determined based on the amplitude of the main pulse Pm, the vibrations of the compressive member 331 can be effectively reduced, because the vibrations can be predicted from the amplitude of the main pulse Pm.

Figure 22A:
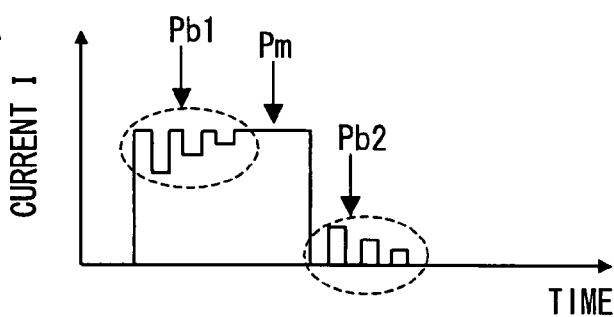
FIG. 22A is a graph showing a modified relationship between the time and the current.

At least one of the pulse amplitude and the pulse period of the brake pulse Pb may be gradually changed. As shown in FIG. 22A, the pulse amplitude may be gradually reduced. When the brake pulse Pb has plural pulses, the pulse amplitude of a latter pulse may be made smaller than that of a former pulse. Usually, the vibrations of the compressive member 331 attenuate and converge, as the compressive member 331 is moved closer to the target position. Therefore, the vibrations of the compressive member 331 can be more effectively reduced, when the pulse amplitude is gradually reduced.

Figure 22B:
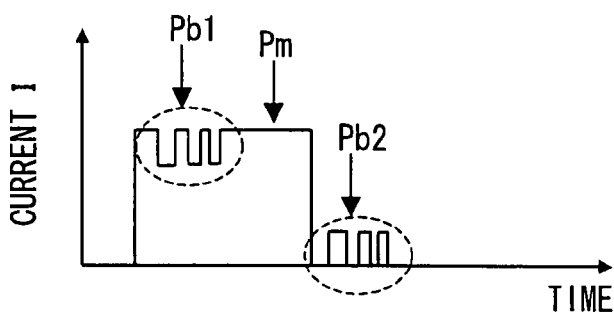
FIG. 22B is a graph showing another modified relationship between the time and the current.

As shown in FIG. 22B, the pulse period may be gradually reduced. When the brake pulse Pb has plural pulses, the pulse period of a latter pulse may be made smaller than that of a former pulse. Usually, a period of the vibrations of the compressive member 331 is gradually decreased, as the compressive member 331 is moved closer to the target position. Therefore, the vibrations of the compressive member 331 can be more effectively reduced, when the pulse period is gradually reduced in accordance with the period of the vibrations of the compressive member 331.

In the 9th embodiment, the other parts may be made similarly to those of the above-described 8th embodiment.

10th Embodiment

Figure 23:
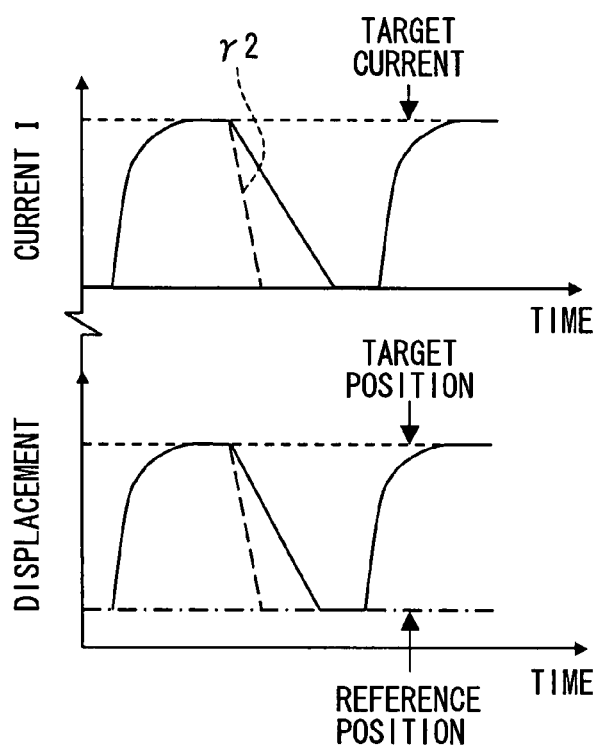
FIG. 23 is a graph showing a relationship between a time and a current, and a displacement of a compressive member of a gaseous constituent supply device according to a 10th embodiment.

As shown in FIG. 23, the compressing portion 330 is displaceable to be synchronized with the current I at both of the rising and the falling of the current I, in a 10th embodiment. Specifically, a change of the current I corresponds to the displacement of the compressing portion 330. That is, the displacement of the compressing portion 330 is capable of following the change of the current I.

Specifically, the current I asymptotically varies relative to a target current at the rising of the current I. That is, current variation is made smaller, when the current I is made closer to the target current. The driving current I is gradually made closer to the target current. Thus, the displacement of the compressive member 331 can be secured to follow the current I. Therefore, the transient distortion can be reduced.

Further, a falling gradient of the driving current I is set smaller than a predetermined second gradient $\gamma 2$. Here, the predetermined second gradient $\gamma 2$ represents a limit gradient, in which the displacement of the compressive member 331 can be synchronized with the falling of the current I.

Thereby, the displacement of the compressive member 331 can be synchronized with the falling of the current I. Because a rapid displacement of the compressive member 331 can be reduced, impact sound (noise) can be reduced. Further, the transient distortion around the reference position can be reduced, because a response of the compressive member 331 is not delayed relative to the falling of the current I.

In a case in which the falling gradient of the current I is equal to the predetermined second gradient $\gamma 2$, the air cannon projectile G may be generated inside of the chamber 320 and emitted into the compartment 2 through the outlet 310A, because the chamber 320 is expanded.

Therefore, when the compressive member 331 is returned to the reference position, the falling gradient of the current I is set smaller than the predetermined second gradient $\gamma 2$, in order to prevent an unnecessary emission of the air cannon projectile G. However, the falling gradient of the current I may be set equal to the predetermined second gradient $\gamma 2$, in order to make successive emissions of the air cannon projectile G.

Figure 24:
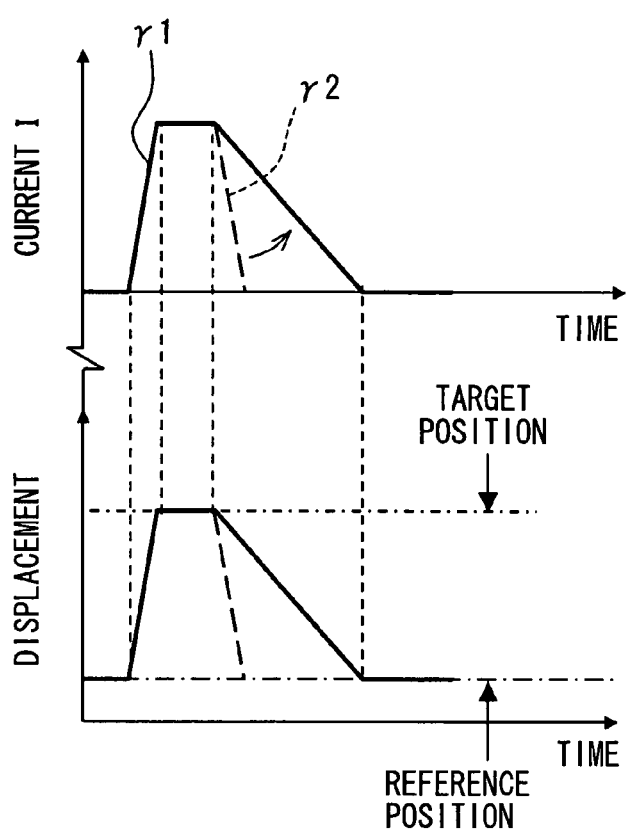
FIG. 24 is a graph showing a modified relationship between the time and the current, and the displacement of the compressive member.

As shown in FIG. 24, a rising gradient of the driving current I may be set to be a predetermined first gradient $\gamma 1$. Here, the first gradient $\gamma 1$ represents a limit gradient, in which the displacement of the compressive member 331 can be synchronized with the rising of the current I. Thereby, the displacement of the compressive member 331 can be synchronized with the rising of the current I. Therefore, the transient distortion of the compressive member 331 around the target position can be reduced, because a response of the compressive member 331 is not delayed relative to the rising of the current I.

However, the rising gradient of the driving current I is not limited to the first gradient $\gamma 1$. The rising gradient of the driving current I may be set smaller than the first gradient $\gamma 1$.

In the 10th embodiment, the other parts may be made similarly to those of the above-described 8th embodiment.

(Modification)

In the above-described 8th to 10th embodiments, the protrusion 351 of the damper 350 is in contact with the entire periphery of the taper 332A of the pressing member 332. Alternatively, the protrusion 351 of the damper 350 may be in contact with a part of the taper 332A of the pressing member 332. Further, the damper 350 may have a bar shape or a thin board shape, other than the membrane shape. Furthermore, the damper 350 may not have the protrusion 351.

Two of the brake pulses Pb1, Pb2 are overlapped with the main pulse Pm. However, only one of the brake pulses Pb1, Pb2 may be overlapped with the main pulse Pm, or three or more brake pulses may be overlapped with the main pulse Pm.

11th Embodiment

An 11th embodiment will be described with reference to FIGS. 25 to 28A. A gaseous constituent supply device emits an air cannon projectile G containing a predetermined gaseous constituent, and is typically mounted to a vehicle 1. The device is constructed with emitting units 10A, 10B, 10C provided in a compartment 2 of the vehicle 1, in order to supply the gaseous constituent to each occupant 3, 4.

Figure 25:
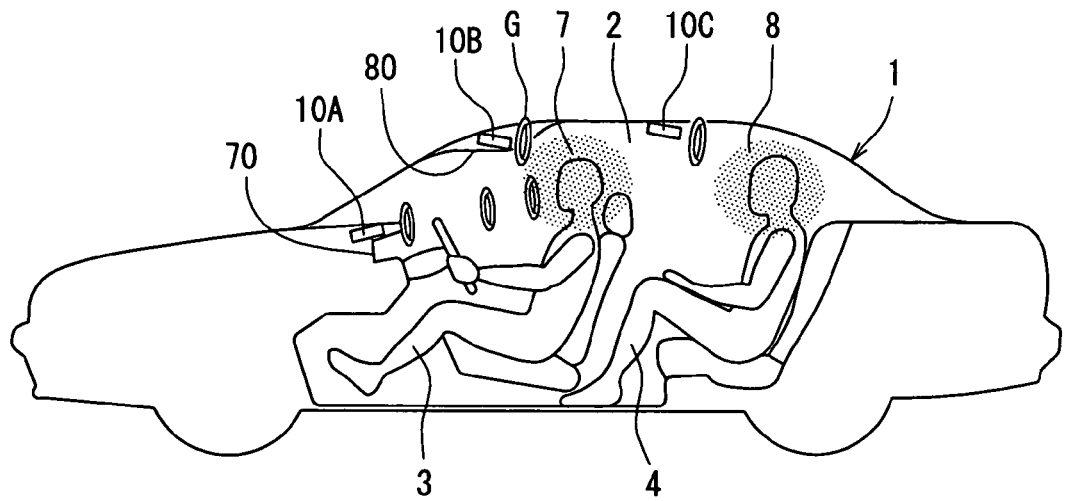
FIG. 25 is a schematic diagram showing an arrangement of emitting units of a gaseous constituent supply device according to a 11th embodiment.

As shown in FIG. 25, the emitting units 10A, 10B are positioned such that the air cannon projectile G can be emitted toward the occupant 3, and the emitting unit 10C is positioned such that the air cannon projectile G can be emitted toward the occupant 4. Specifically, the emitting unit 10A is disposed in an instrument panel 70, and the emitting unit 10B is disposed in an overhead module 80 on a front seat side ceiling part. The emitting units 10A, 10B emit the air cannon projectile G toward the occupant 3. In contrast, the emitting unit 10C is disposed on a rear seat side ceiling part, and emits the air cannon projectile G toward the occupant 4.

The air cannon projectile G represents a fluid mass, which is pushed out of a space through an emitting hole of the space, after a fluid in the space is compressed. The fluid mass is formed into a vortex ring shape or sphere shape, for example. When the air cannon projectile G hits a body, e.g., face or shoulder, of the occupant 3, 4, the fluid mass of the air cannon projectile G collapses, and the gaseous constituent contained in the air cannon projectile G diffuses in a diffusion area 7, 8.

Figure 26:
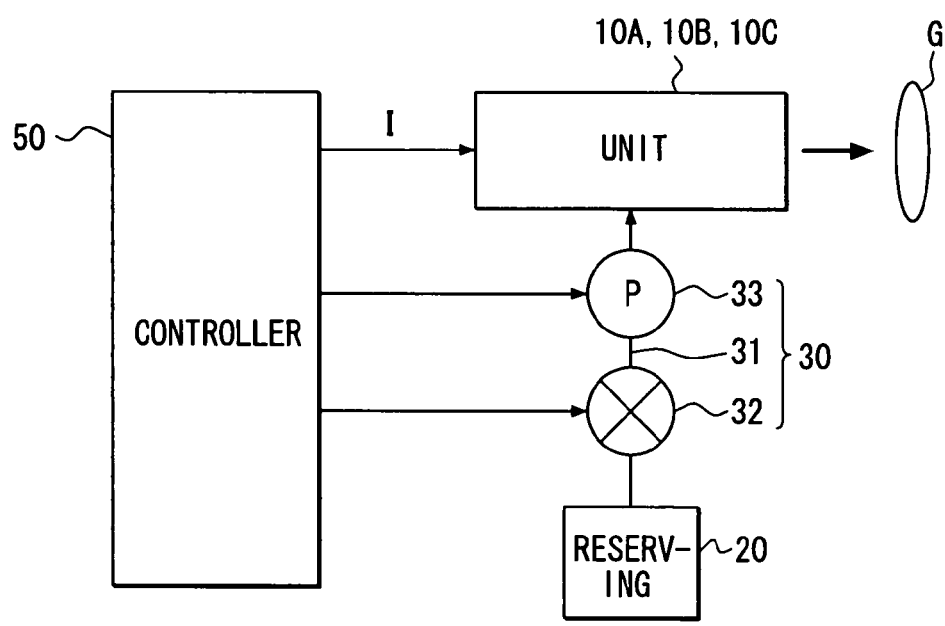
FIG. 26 is a block diagram showing a construction of the device of the 11th embodiment.

As shown in FIG. 26, a conveying portion 30 supplies the gaseous constituent stored in a reserving portion 20 to the emitting units 10A, 10B, 10C. The reserving portion 20 is constructed with a tank, in which a predetermined gaseous constituent, e.g., moisture or perfume, is stored. The conveying portion 30 includes a connecting tube 31, a valve 32 and a pump 33. The connecting tube 31 connects the reserving portion 20 to a gaseous constituent chamber 420 (to be described below) in the emitting unit 10A, 10B, 10C. The valve 32 opens and closes the connecting tube 31. The pump 33 sends the gaseous constituent from the reserving portion 20 into the chamber 420.

The valve 32 opens and closes the connecting tube 31 in response to a driving signal output from a controller 50 (to be described below). When the valve 32 opens the connecting tube 31, the gaseous constituent flows from the reserving portion 20 into the connecting tube 31. Similarly, the pump 33 operates in response to a driving signal output from the controller 50. The pump 33 sends the gaseous constituent from the connecting tube 31 into the chamber 420.

Figure 27:
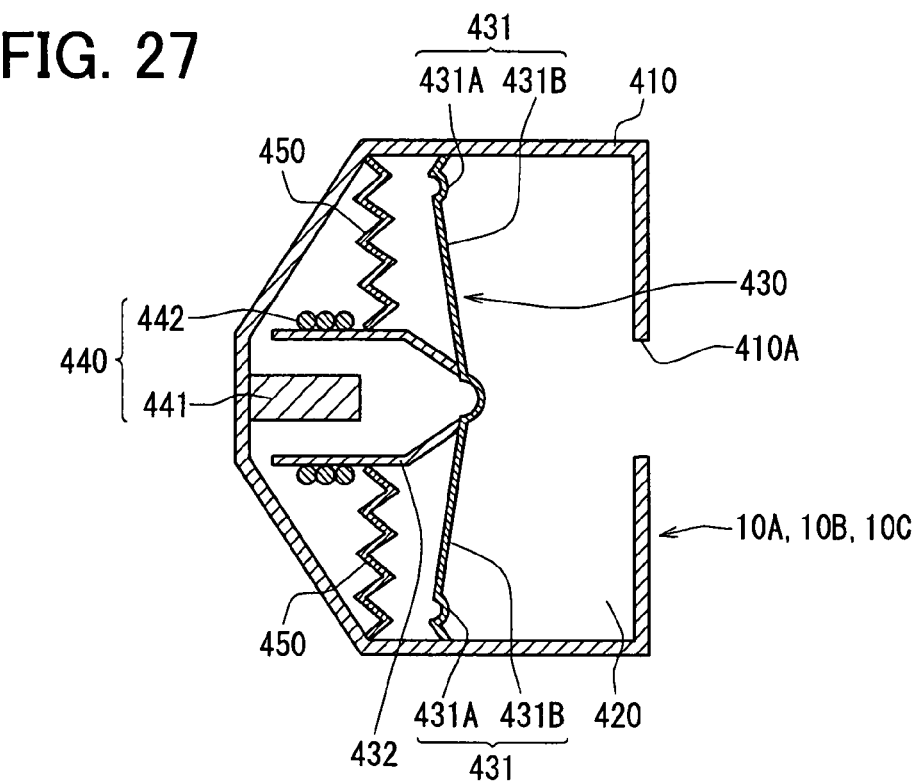
FIG. 27 is a cross-sectional view showing the emitting unit in which a compressive member is positioned at a reference position.

As shown in FIG. 27, the emitting unit 10A, 10B, 10C includes the chamber 420, a compressing portion 430, a driving portion 440 and a supporting portion 450 in a case 410. The chamber 420 holds the gaseous constituent therein. The compressing portion 430 is constructed with a compressive member 431 and a pressing member 432, and compresses air in the chamber 420. The driving portion 440 drives the compressing portion 430. The supporting portion 450 supports the pressing member 432 of the compressing portion 430.

The case 410 has a cylinder shape, for example, and has an air cannon projectile emitting outlet 410A in a front face of the case 410. The air cannon projectile G is emitted from the case 410 through the emitting outlet 410A into the compartment 2. The chamber 420 is connected to the reserving portion 20 by the connecting tube 31, and supplied with the gaseous constituent by the valve 32 and the pump 33. Thus, the chamber 420 holds air containing the gaseous constituent.

The compressing portion 430 is positioned to face the emitting outlet 410A. The compressive member 431 of the compressing portion 430 is displaceable toward the emitting outlet 410A (front side), and the pressing member 432 of the compressing portion 430 presses the compressive member 431.

Figure 28A:
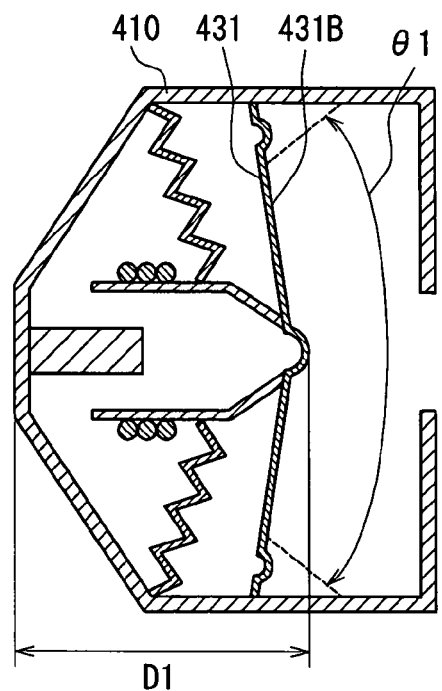
FIG. 28A is a cross-sectional view showing the emitting unit in which the compressive member is positioned at a compression position.

The compressive member 431 has an approximately round shape, and a periphery of the compressive member 431 is fixed to an inner surface of the case 410. Because the periphery of the compressive member 431 has an edge 431A, the compressive member 431 is displaceable in a front-and-rear direction. The compressive member 431 shown in FIG. 27 is in a reference position, in which the compressive member 431 is spaced from the emitting outlet 410A by a predetermined dimension. The compressive member 431 can be displaced toward the emitting outlet 410A (compression side) so as to compress air in the chamber 420. When the compressive member 431 is compressed, the compressive member 431 is in a compression position, as shown in FIG. 28A. Thereby, the air cannon projectile G containing the gaseous constituent can be emitted through the emitting outlet 410A.

When the compressive member 431 is in the reference position shown in FIG. 27, an approximately center area of the compressive member 431 is protruded toward the front (compression) side from a peripheral area of the compressive member 431. The compressive member 431 has a compression face 431B corresponding to a front face of the approximately center area of the compressive member 431. An approximately center part of the compression face 431B is protruded toward the compression side from a peripheral part of the compression face 431B. Specifically, the compression face 431B has an approximately conical surface protruding toward the compression side.

The pressing member 432 has a cylinder shape, and has a front end and a base end. A coil 442 of the driving portion 440 is twisted around the base end of the pressing member 432. The front end of the pressing member 432 is integrated with the compressive member 431. An external diameter of the front end of the pressing member 432 is made smaller than an internal diameter of the compressive member 431. The front end of the pressing member 432 is integrated with the center area of the compressive member 431.

The driving portion 440 includes a pair of a magnet 441 and the coil 442. The magnet 441 is fixed to an inner rear face of the case 410, and the coil 442 is integrated with the pressing member 432. The magnet 441 has a cylinder shape, and protrudes toward the front side from the inner rear face of the case 410. The magnet 441 is positioned at a rear side of an inner space of the pressing member 432. Because the coil 442 is twisted around the base end of the pressing member 432, the coil 442 is positioned so as to surround the magnet 441. The coil 442 of the emitting unit 10A, 10B, 10C is supplied with a driving current I from the controller 50, as shown in FIG. 26.

When the coil 442 is supplied with the driving current I, the magnet 441 generates a magnetic field. Then, a Lorentz force is formed by the magnetic field. Due to the Lorentz force, the coil 442 is biased toward the front side. Thereby, the pressing member 432 integrated with the coil 442 presses the compressive member 431. Thus, the compressive member 431 can be displaced from the reference position shown in FIG. 27 to the compression position shown in FIG. 28A. In contrast, when the supply of the driving current I is stopped, the compressive member 431 and the pressing member 432 return to the reference position, because the bias force is not generated.

The driving current I has a predetermined wave shape so as to generate the air cannon projectile G. For example, the driving current I is a rectangular-wave current. Because a power of the Lorentz force is determined based on amplitude of the rectangular-wave of the current I, a displacement dimension of the compressive member 431 can be determined based on the amplitude of the rectangular-wave of the current I.

The supporting portion 450 supports the pressing member 432, and is formed by folding a membrane material into a wave shape. The supporting portion 450 has a ring shape, corresponding to the shapes of the case 410 and the pressing member 432. An outer end of the supporting portion 450 is fixed to an inner surface of the case 410, and an inner end of the supporting portion 450 is fixed to the pressing member 432. The supporting portion 450 can support the pressing member 432, even when the pressing member 432 is displaced, because the supporting portion 450 has the wave shape. The inner end of the supporting portion 450 can be displaced together with the pressing member 432.

The controller 50 controls the valve 32, the pump 33 and the driving current I supplied to the coil 442, as shown in FIG. 26. For example, a detecting sensor for detecting a concentration of the gaseous constituent is disposed in the compartment 2, and the controller 50 controls the valve 32, the pump 33 and the driving current I based on the concentration of the gaseous constituent. Specifically, when the concentration of the gaseous constituent in the compartment 2 is equal to or lower than a predetermined value, the controller 50 determines that the gaseous constituent is insufficient in the compartment 2. Then, the controller 50 opens the valve 32, actuates the pump 33 and supplies the driving current I to the coil 442, so as to emit the air cannon projectile G.

Next, operation of the device will be described. The controller 50 controls the valve 32, the pump 33 and the driving current I, so as to timely emit the air cannon projectile G. That is, the controller 50 opens the valve 31 and actuates the pump 33 so as to supply the gaseous constituent to the chamber 420. Then, the controller 50 supplies the driving current I to the coil 442 such that the pressing member 432 presses the compressive member 431 toward the front side.

Thereby, the compressive member 431 is displaced from the reference position to the compression position, in order to compress air in the chamber 420. Thus, the air cannon projectile G containing the gaseous constituent is emitted toward the occupant 3, 4 through the emitting outlet 410A. Here, when the compressive member 431 is displaced from the reference position to the compression position, impact noise is generated, because air in the chamber 420 is compressed. The impact noise may be emitted toward the occupant 3, 4 through the outlet 410A.

In the 11th embodiment, because the compression face 431B of the compressive member 431 is protruded to the compression (front) side, a directional angle of the impact noise is large, compared with a case in which the compression face 431B of the compressive member 431 is protruded toward the rear side. That is, the impact noise can be diffused into a wide area.

Specifically, as shown in FIG. 28A, when the compression face 431B of the compressive member 431 is protruded toward the front side, a directional angle θ1 of the impact noise is large. Thereby, because the impact noise can be diffused, a sound pressure of the impact noise can be low. Thus, the impact noise has a less impact relative to the occupant 3, 4. In contrast, as shown of a comparison example in FIG. 28B, when the compression face 431B of the compressive member 431 is protruded to the rear side, a directional angle θ2 of the impact noise is narrow and small. Thereby, because the impact noise is concentrated toward the outlet 410A, a sound pressure of the impact noise is high. Thus, in this comparison example, the impact noise is excessively transmitted to the occupant 3, 4.

According to the 11th embodiment, because the compression face 431B of the compressive member 431 is protruded toward the front side, the sound pressure of the impact noise can be lowered. Thus, the impact noise has a less impact relative to the occupant 3, 4.

Figure 28B:
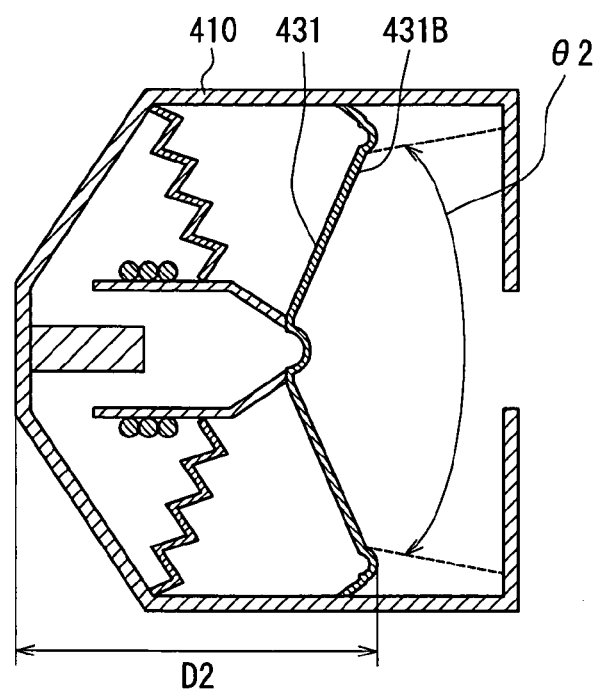
FIG. 28B is a cross-sectional view showing an emitting unit of a comparison example in which a compressive member is positioned at the compression position.

Further, because the compression face 431B of the compressive member 431 is protruded toward the front side, the compressive member 431 and the pressing member 432 can be overlapped with each other in the front-and-rear direction. Thereby, as shown in FIGS. 28A and 28B, a dimension D1 between a rear end of the case 410 and a front end of the compressive member 431 can be made smaller than a dimension D2 between the rear end of the case 410 and the front end of the compressive member 431. Therefore, a size of the unit 10A, 10B, 10C can be reduced, because a dimension of the case 410 in the front-and-rear direction can be reduced.

Further, because the pressing member 432 presses the center area of the compressive member 431, the compressive member 431 is displaced toward the front side, keeping a state that the center area of the compressive member 431 is protruded toward the front side. Therefore, when the compressive member 431 is displaced toward the front side, the compressive member 431 can be restricted from being deformed toward the rear side. Thus, the impact noise can be appropriately diffused.

Further, because the compression face 431B of the compressive member 431 has the conical surface, the impact noise can be diffused toward whole directions perpendicular to the front-and-rear direction. Therefore, because the impact noise can be effectively diffused, the impact noise is less transmitted to the occupant 3, 4.

Figure 29:
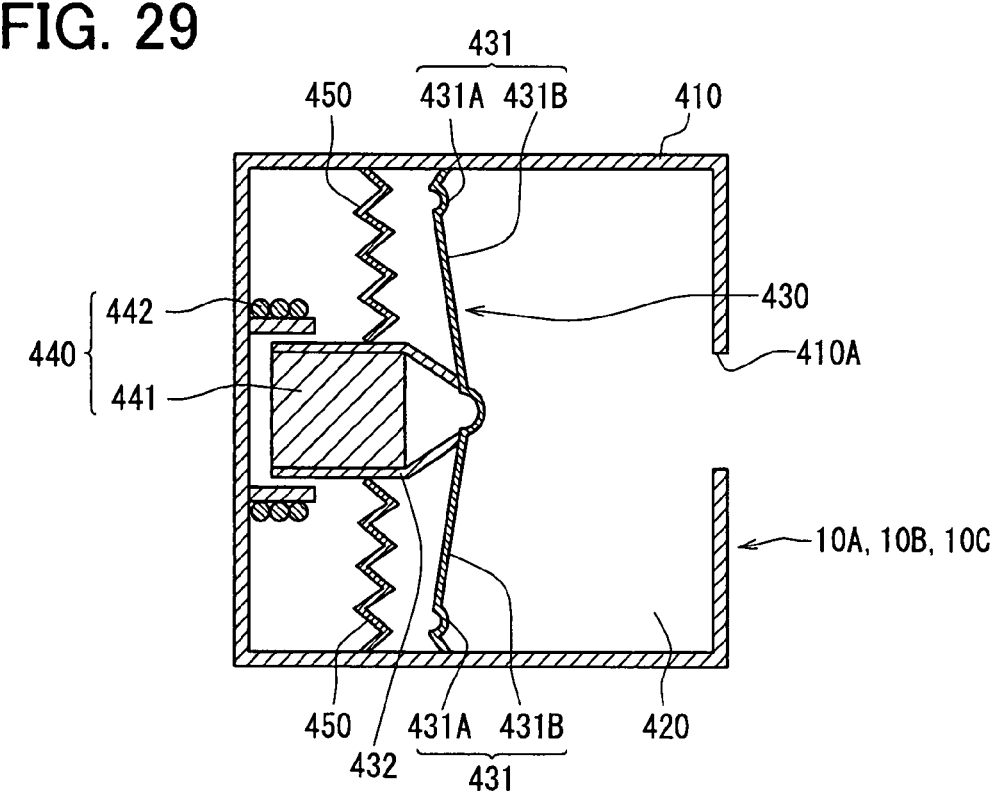
FIG. 29 is a cross-sectional view showing a modification of the emitting unit of the 11th embodiment.

In the 11th embodiment, the magnet 441 is fixed to the inner rear face of the case 410, and the coil 442 is integrated with the pressing member 432. Alternatively, as shown in FIG. 29, the coil 442 may be fixed to the case 410, and the magnet 441 may be integrated with the pressing member 432. In this case, the Lorentz force is generated by supplying the driving current I to the coil 442. Then, the pressing member 432 integrated with the magnet 441 is biased toward the front side, due to the Lorentz force. Thus, the compressive member 431 can be displaced toward the compression side.

Further, in this case, because a weight of the compressing portion 430 is increased, a rapid displacement of the compressive member 431 can be reduced. Thus, the impact noise can be reduced. Furthermore, a transient distortion can be effectively reduced. The transient distortion represents vibrations of the compressive member 431 around a target position (the reference position or the compression position). The vibrations are caused, when the compressive member 431 cannot sufficiently correspond to a rising (falling) of the driving current I.

12th Embodiment

Figure 30:
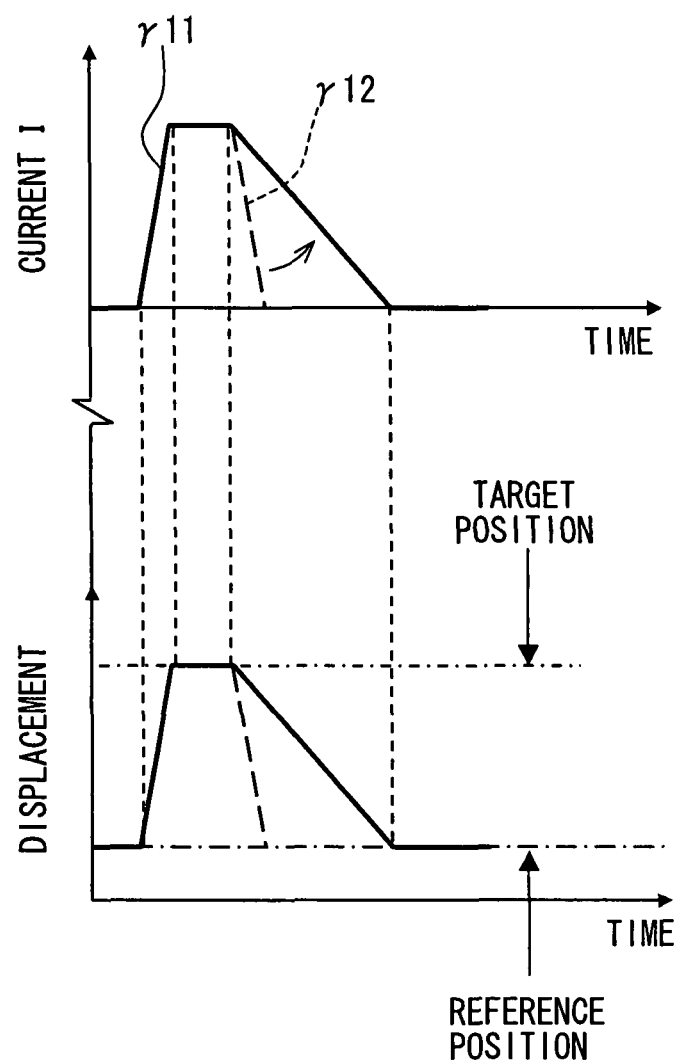
FIG. 30 is a graph showing a relationship between a time and a current, and a displacement of a compressive member of a gaseous constituent supply device according to a 12th embodiment.

A 12th embodiment will be described with reference to FIG. 30. A compressing portion 430 is displaceable to be synchronized with a wave shape of a rising and/or a falling of a driving current I. That is, a displacement of the compressing portion 430 can correspond to the rising and/or the falling of the driving current I. The displacement of the compressing portion 430 can follow the rising and/or the falling of the driving current I.

Specifically, a rising gradient of the driving current I is set to a predetermined first gradient γ11. Here, the first gradient γ11 represents a limit gradient that the displacement of the compressive member 431 can be synchronized with the rising of the driving current I. That is, the first gradient γ11 represents a limit gradient that the displacement of the compressive member 431 can follow the rising of the driving current I.

Because the displacement of the compressive member 431 is synchronized with the rising of the driving current I, impact noise can be reduced. The impact noise is caused by a rapid displacement of the compressive member 431, when the compressive member 431 cannot follow the rising of the driving current I. Further, a transient distortion can be reduced. The transient distortion represents vibrations of the compressive member 431 around a target position, which are caused by a correspondence delay of the compressive member 431 relative to the rising of the driving current I.

Further, a falling gradient of the driving current I is set smaller than a predetermined second gradient γ12. Here, the second gradient γ12 represents a limit gradient that the displacement of the compressive member 431 can be synchronized with the falling of the driving current I. That is, the predetermined second gradient γ12 represents a limit gradient that the displacement of the compressive member 431 can follow the falling of the driving current I.

Thereby, because the displacement of the compressive member 431 can be synchronized with the falling of the driving current I, impact noise can be reduced. The impact noise is caused by a rapid displacement of the compressive member 431, when the compressive member 431 cannot follow the falling of the driving current I. Further, a transient distortion can be reduced. The transient distortion represents vibrations of the compressive member 431 around a reference position, which are caused by a correspondence delay of the compressive member 431 relative to the falling of the driving current I.

In a case in which the falling gradient of the driving current I is set to the second gradient γ12, the air cannon projectile G may be generated inside of the chamber 420, because the chamber 420 is expanded. Further, the air cannon projectile G generated inside of the chamber 420 may be emitted to the compartment 2 through the outlet 410A.

Therefore, when the compressive member 431 is returned to the reference position, the falling gradient of the driving current I is set smaller than the second gradient γ12, in order to prevent an unnecessary emission of the air cannon projectile G. However, the falling gradient of the driving current I may be set to the second gradient γ12, in order to make successive emissions of the air cannon projectile G.

In the 12th embodiment, the other parts can be made similarly to those of the above-described 11th embodiment.

(Modification)

In the 11th and 12th embodiments, the outlet 410A is positioned at the front face of the case 410, and the compressive member 431 is positioned to face the outlet 410A. However, the outlet 410A may be positioned at a side face of the case 410.

The compression face 431B has the conical surface protruding toward the front side. Alternatively, the compression face 431B may have a revolutionary hyperboloid shape or a revolutionary paraboloid shape, for example.

The rising gradient of the driving current I is set to the first gradient γ11 in the 12th embodiment. However, the rising gradient of the driving current I may be set smaller than the first gradient γ11.

Figure 31:
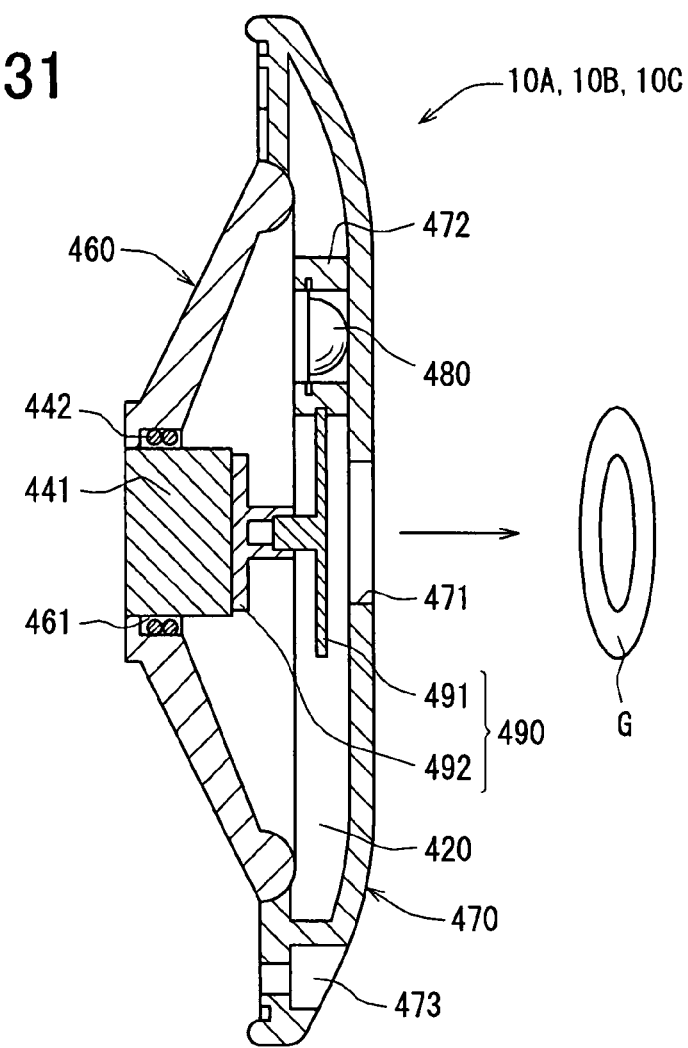
FIG. 31 is a cross-sectional view showing another gaseous constituent supply device of a modification of the 11th and 12th embodiments.

In addition, as shown in FIG. 31, the gaseous constituent supplying unit 10A, 10B, 10C may include an actuator 460, a covering member 470, a gaseous constituent generating cartridge 480 and a shutter mechanism 490. The actuator 460 is covered with the covering member 470, and the gaseous constituent chamber 420 is formed between the actuator 460 and the covering member 470.

The covering member 470 has an emitting outlet 471 for emitting the air cannon projectile G, and the emitting outlet 471 is positioned to face the actuator 460. The gaseous constituent generating cartridge 480 is disposed in the covering member 470, and holds the predetermined gaseous constituent in a volatile state. The cartridge 480 is supported by a supporting part 472 of the covering member 470. Thereby, the gaseous constituent can be supplied to the chamber 420 from the cartridge 480.

The actuator 460 has an aperture 461 passing through its approximately center part, and the coil 442 is twisted and fixed to an inner surface of the aperture 461. Further, the magnet 441 paired with the coil 442 is disposed in the aperture 461 through a clearance from the coil 442. When the coil 442 is supplied with the driving current I, the actuator 460 is displaced toward the outlet 471 (front side). Then, air in the chamber 420 is compressed, and the air cannon projectile G is emitted from the chamber 420 through the outlet 471.

The shutter mechanism 490 opens and closes the outlet 471, and is disposed in the chamber 420. The shutter mechanism 490 includes a shutter 491 and a supporting part 492. The shutter 491 is moved together with the actuator 460 toward the outlet 472 in order to close the outlet 471. The supporting part 492 supports the shutter 491 such that the shutter 491 can be moved toward the outlet 472. When the shutter 491 is in a rear position, the air cannon projectile G is enabled to be emitted, because the outlet 471 is open. When the shutter 491 is in a front position, the air cannon projectile G is disabled to be emitted, because the outlet 471 is closed.

Further, the covering member 470 has a screw hole 473. The unit 10A, 10B, 10C can be fixed to a bracket of the vehicle 1, for example, by screwing.

13th Embodiment

Figure 32:
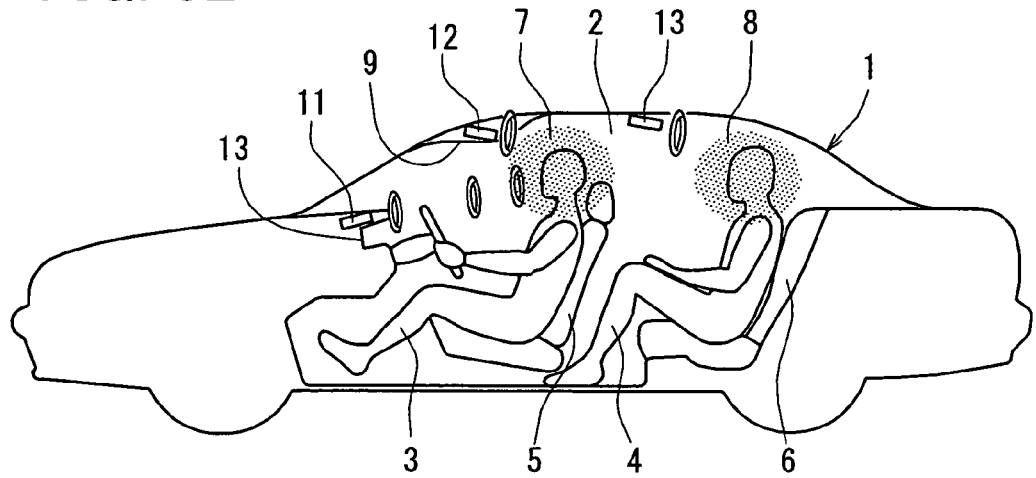
FIG. 32 is a schematic diagram showing an arrangement of a gaseous constituent supply device according to 13th-17th embodiments.

A 13th embodiment will be described with reference to FIGS. 32-34B. As shown in FIG. 32, gaseous constituent supply devices 11, 12, 13 are disposed in a compartment 2 of a vehicle 1. As shown in FIG. 34A, each of the gaseous constituent supply devices 11, 12, 13 includes a case 520 having a first chamber 521 and a second chamber 522 therein.

An air (i.e., fluid) mass in the second chamber 522 is compressed, and pushed out of the second chamber 522 through an emitting outlet 524. The air mass is formed into a vortex ring shape or sphere shape, for example. The air mass contains a predetermined gaseous constituent, and is emitted toward an occupant 3, 4 or a space in the compartment 2. Then, the air mass is diffused so as to provide the predetermined gaseous constituent to the occupant 3, 4.

Because the gaseous constituent is contained in the air mass, the gaseous constituent is difficult to be affected by air flow from an air-conditioning device (not shown). Further, the gaseous constituent corresponds to a feeling or psychology of the occupant 3, 4, which is affected by a traffic condition, e.g., traffic jam or stoplight, a high-speed driving or an urban-area driving, for example.

The gaseous constituent supply device 11, 12, 13 is widely used in a private vehicle or business vehicle, and supplies the occupant 3, 4 with the air mass containing the predetermined gaseous constituent. As shown in FIG. 32, the devices 11, 12, 13 are positioned such that the air mass can be accurately emitted toward the occupant 3, 4 in the compartment 2 of the vehicle 1.

Specifically, the device 11 is disposed in an instrument panel 13 such that the air mass can be emitted into the compartment 2. An air-conditioning device (not shown) is usually disposed in the instrument panel 13. The device 11 may be disposed adjacent to the air-conditioning device, or the device 11 may be integrated with the air-conditioning device.

Air mass is emitted from the device 11, and passes through a grill opening of the instrument panel 13 toward a face area of the occupant 3 on a front seat 5. Then, the air mass hits the body, e.g., face or shoulder, of the occupant 3. The air mass collapses, and the gaseous constituent contained therein diffuses in a diffusion area 7. Therefore, the occupant 3 can take in the gaseous constituent through a nose or mouth.

The device 12 is disposed in an overhead module 9 on a front seat side ceiling part in the compartment 2. Air mass is emitted from the device 12, and passes through an opening of the overhead module 9 toward the face of the occupant 3 on the front seat 5. Then, the air mass hits the body, e.g., face or head, of the occupant 3. The air mass collapses, and the gaseous constituent contained therein diffuses in the diffusion area 7. Therefore, the occupant 3 can take in the gaseous constituent through the nose or mouth.

The device 13 is disposed on a rear seat side ceiling part in the compartment 2. Air mass is emitted from the device 12 toward a face of the occupant 4 on a rear seat 6. Then, the air mass hits the body, e.g., face or head, of the occupant 4. The air mass collapses, and the gaseous constituent contained therein diffuses in a diffusion area 8. Therefore, the occupant 4 can take in the gaseous constituent through a nose or mouth.

The predetermined gaseous constituent provides the occupant 3, 4 with comfortability or awakefullness. For example, the predetermined gaseous constituent includes moisture, perfume, oxygen, aroma, collagen, antiallergic component, ion, coolness or warmness. At least one of them is stored in the first chamber 521 of the device 11, 12, 13 in advance.

The moisture eases dryness of mucous membrane for a nostril or throat of the occupant 3, 4. When the occupant 3, 4 takes in the perfume, the aroma or the ion through the nose, the occupant 3, 4 can be relaxed.

The perfume, the oxygen or the coolness decreases sleepiness of the occupant 3, 4, that is, provides awakeness to the occupant 3, 4. The coolness locally provides a cool effect to the occupant 3, 4 in a hot condition, and the warmness locally provides a warm effect to the occupant 3, 4 in a cold condition. When a skin lotion in a volatile state is contained in the air mass, a skin of the occupant 3, 4 can be moisturized. Thus, the gaseous constituent is effective for a health or beauty of the occupant 3, 4.

The device 11, 12, 13 may have a flat shape so as to be disposed in a narrow space in the instrument panel 13 or the overhead module 9, or on the ceiling part of the compartment 2.

An operation of the device 11, 12, 13 will be described with reference to FIG. 33. A compressing portion 523 of the device 11, 12, 13 is controlled in response to signals output from a gaseous constituent supply electric control unit (supply ECU) 100. The supply ECU 100 analyzes signals output from a vehicle integration electric control unit (vehicle ECU) 102 and an operation panel 101, and determines an emitting condition of the air mass, e.g., timing or speed.

The supply ECU 100 controls the compressing portion 523 of the device 11, 12, 13 based on the determination of the emitting condition of the air mass. For example, the supply ECU 100 controls a timing for sending the predetermined gaseous constituent from the first chamber 521 into the second chamber 522, or a timing for compressing air in the second chamber so as to emit the air mass from the second chamber 522 though the emitting outlet 524.

The supply ECU 100 controls an actuation and a compressing power for the compressing portion 523. For example, due to the control of the compressing power of the compressing portion 523, the compressing portion 523 can emit the air mass toward a target occupant or position. Due to the control of the actuation of the compressing portion 523, the compressing portion 523 can emit the air mass successively or intermittently.

Further, in a case in which plural devices 11, 12, 13 are disposed in the compartment 2, as shown in FIG. 32, the supply ECU 100 can actuate only one of the devices 11, 12, 13 or some of the devices 11, 12, 13 at the same time.

The vehicle ECU 102 is supplied with information for operations of functional parts in the vehicle 1, and communicates with the supply ECU 100. For example, the information includes a vehicle speed, a brake state, a distance between the vehicle 1 and the front vehicle, or a window state, e.g., open or close. The vehicle ECU 102 sends the information to the supply ECU 100.

When the vehicle speed is equal to or lower than a predetermined value, when a braking number per unit time is equal to or larger than a predetermined value, or when the distance between the vehicle 1 and the front vehicle is equal to or smaller than a predetermined value, the supply ECU 100 determines that the vehicle 1 is in a traffic jam. Then, the supply ECU 100 controls the air mass containing the perfume, the oxygen or the coolness to be emitted toward the occupant 3, i.e., a driver, in order to provide awakeness effect to the occupant 3. Alternatively, the supply ECU 100 controls the air mass containing the perfume, the aroma or the ion to be emitted toward the occupant 3, in order to provide relax effect to the occupant 3.

When the vehicle speed is kept to be equal to or larger than a predetermined value (e.g., 80 km/h) for a predetermined period, the supply ECU 100 determines that the vehicle 1 is driving on a high-speed way. Then, the supply ECU 100 controls the air mass containing the perfume, the oxygen or the coolness to be emitted toward the occupant 3, in order to provide awakeness effect to the occupant 3.

When the vehicle ECU 102 sends the supply ECU 100 with information that the window is kept to be open, the supply ECU 100 determines that outside air blows into the compartment 2. Then, the supply ECU 100 disables the emission of the air mass for a predetermined period or until when the vehicle ECU 102 sends the supply ECU 100 with information that the window is closed. When the window is open, it is difficult to diffuse the air mass toward a predetermined occupant or space, because the outside air blows into the compartment 2. Therefore, the emission of the air mass is limited, when the window is open.

The operation panel 101 is used for forcibly actuating the compressing portion 523, when the occupant 3, 4 wants the predetermined gaseous constituent. For example, the operation panel 101 includes a switch or button on the instrument panel 13. Due to the operation panel 101, the occupant 3, 4 can actuate the compressing portion 523, and the occupant 3, 4 can control an amount and a direction of the air mass.

Next, a construction of the device 11, 12, 13 will be described with reference to FIGS. 34A and 34B. The case 520 has the emitting outlet 524, through which the air mass is emitted. An inner space of the case 520 is separated into the first chamber 521 and the second chamber 522. The second chamber 522 communicates with the emitting outlet 524, and the first chamber 521 holds a predetermined gaseous constituent therein. A communication part 526 and the compressing portion 523 are provided between the first chamber 521 and the second chamber 522. The communication part 526 makes the first chamber 521 and the second chamber 522 to communicate with each other. The compressing portion 523 compresses air in the second chamber 522 so as to emit the air mass to the compartment 2.

The gaseous constituent is sent from the first chamber 521 to the second chamber 522 through the communication part 526 by an operation of the compressing portion 523. The case 520 is made of an airtight material for reducing a leak of the gaseous constituent. For example, the case 520 is made of resin or metal. However, the material of the case 520 is not limited to the resin of metal.

The first chamber 521 has the predetermined gaseous constituent therein in advance, and the compressing portion 523 changes a volume of the first chamber 521. The gaseous constituent is volatile, and the first chamber 521 is filled with the volatile gaseous constituent. Usually, the gaseous constituent is sealed in the first chamber 521 by the compressing portion 523.

The second chamber 522 is filled with air sucked from the compartment 2 through the emitting outlet 524, and the compressing portion 523 changes a volume of the second chamber 522. When air in the second chamber 522 is compressed by the compressing portion 523, the air mass is emitted from the second chamber 522 into the compartment 2 through the emitting outlet 524. At the same time, the gaseous constituent may flow into the second chamber 522 through the communication part 526 from the first chamber 521 in accordance with the operation of the compressing portion 523.

The compressing portion 523 has a board shape, and is displaceable toward the outlet 524 (front side). The compressing portion 523 is displaced toward the front side or the rear side by the supply ECU 100. Thereby, air in the first chamber 521 or air in the second chamber 522 is compressed by the compressing portion 523. Moreover, the compressing portion 523 supports one end of a reverse-flow preventing door 525.

The communication part 526 can be opened and closed by the door 525. The communication part 526 is an aperture provided in the compressing portion 523. Due to the communication part 523, the first chamber 521 and the second chamber 522 can communicate with each other. The door 525 can freely adjust an area of the aperture.

As shown of a chained arrow in FIG. 34A, when the compressing portion 523 is moved toward the outlet 524 (front side), the door 525 closes the communication part 526. Thus, the gaseous constituent in the second chamber 522 is restricted from flowing into the first chamber 521 through the communication part 526.

At this time, a part of the air in the second chamber 522 is emitted into the compartment 2 through the outlet 524 as the air mass, due to an instantaneous decrease in a volume of the second chamber 522. In addition, the door 525 is disposed in the second chamber 522. When the door 525 is opened, the door 525 is moved within the second chamber 522.

Figure 34A:
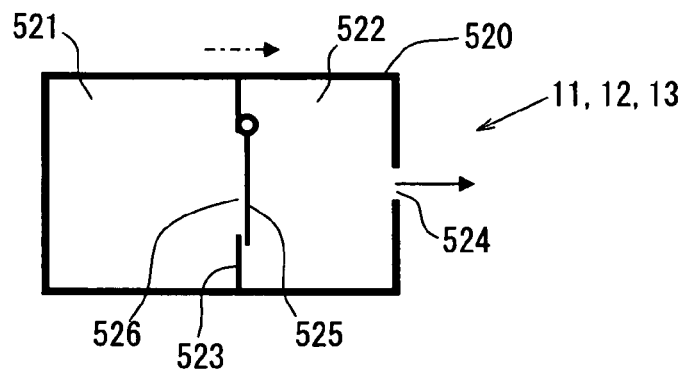
FIG. 34A is a schematic diagram showing the device in which an air mass is emitted.
Figure 34B:
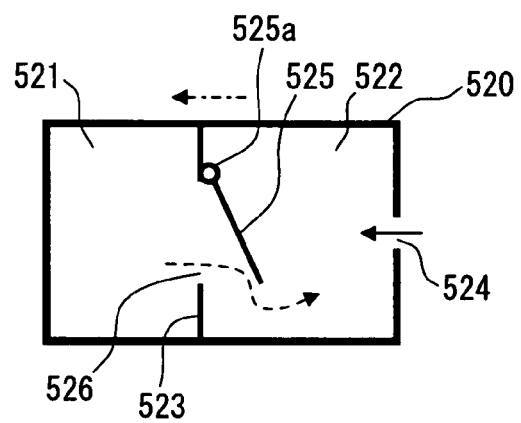
FIG. 34B is a schematic diagram showing the device in which a gaseous constituent is supplied to a second chamber according to the 13th embodiment.

After the air mass is emitted, as shown of a chained arrow in FIG. 34B, the compressing portion 523 is moved toward the rear side in order to compress air in the first chamber 521. At this time, because a pressure in the first chamber 521 becomes high, the door 525 is opened about a support axis 525a within the second chamber 522. Thus, the communication part 526 is opened. Then, as shown of a dashed arrow in FIG. 34B, the gaseous constituent flows from the first chamber 521 into the second chamber 522 through the communication part 526.

The air mass can be supplied to the occupant 3, 4 by repeating the operations shown in FIGS. 34A and 34B. The device 11, 12, 13 has a simple structure without any supplying portion for supplying the gaseous constituent to the second chamber 522. That is, the device 11, 12, 13 has the case 520 and the compressing portion 523 separating the inner space of the case 520 into the first chamber 521 and the second chamber 522. The gaseous constituent in the first chamber 521 is sent to the second chamber 522 through the communication part 526 by the compressing portion 523.

According to the 13th embodiment, because the first chamber 521, the second chamber 522 and the compressing portion 523 can be integrated in the case 520, a size of the device 11, 12, 13 can be made smaller. Usually, the instrument panel 13, the overheat module 9 or the rear seat side ceiling part has a limited height and a limited lateral dimension. Therefore, the small-sized device 11, 12, 13 can be useful for its positioning. Further, because the gaseous constituent in the first chamber 521 is sent to the second chamber 522 through the communication part 526 by the compressing portion 523, any supplying portion for supplying the gaseous constituent to the second chamber 522 is not needed. Thus, the number of parts of the device 11, 12, 13 can be reduced.

Further, the door 525 prevents air from moving from the second chamber 522 into the first chamber 521, when the compressing portion 523 compresses air in the second chamber 522. Therefore, air in the second chamber 522 can be prevented from leaking into the first chamber 521, and a pressure in the second chamber 522 can be appropriately increased. Thus, the air mass can be stably emitted into the compartment 2.

Further, when the door 525 is disposed on the compressing portion 523, a size of the device 11, 12, 13 can be reduced, because an arrangement space for the door 525 is reduced.

Further, when the compressing portion 523 compresses air in the first chamber 521, the door 525 is opened such that the gaseous constituent flows from the first chamber 521 into the second chamber 522 through the communication part 526. Therefore, the door 525 enables the gaseous constituent in the first chamber 521 to be supplied to the second chamber 522, when the compressing portion 523 compresses air in the first chamber 521, in addition to the reverse-flow preventing effect.

14th Embodiment

A gaseous constituent supply device 11, 12, 13 in a 14th embodiment will be described with reference to FIGS. 32, 33, 35A-35D. The device 11, 12, 13 includes a case 530, and an emitting outlet 533 is provided in a front face of the case 530. An air mass is emitted from the case 530 into a compartment 2 of a vehicle 1 through the emitting outlet 533. An inner space of the case 530 is separated into a first chamber 531 and a second chamber 532. The second chamber 532 communicates with the outlet 533, and the first chamber 531 is positioned at a rear side of the case 530. The first chamber 531 holds a predetermined gaseous constituent therein. The device 11, 12, 13 further includes a compressing portion 534 and a communication part 535 in the case 530. The communication part 535 makes the first chamber 531 and the second chamber 532 to communicate with each other, and the compressing portion 534 decreases a volume of the first chamber 531 or the second chamber 532.

The compressing portion 534 separates the inner space of the case 530 into the first chamber 531 and the second chamber 532. The gaseous constituent in the first chamber 531 is sent to the second chamber 532 through the communication part 535 by an operation of the compressing portion 534.

The first chamber 531 holds the predetermined gaseous constituent in advance, and the compressing portion 534 changes a volume of the first chamber 531. The gaseous constituent is volatile, and the first chamber 531 is filled with the volatile gaseous constituent. Usually, the gaseous constituent is sealed in the first chamber 531 by the compressing portion 534.

The second chamber 532 is filled with air sucked from the compartment 2 through the outlet 533, and the compressing portion 534 changes the volume of the second chamber 532. When the compressing portion 534 compresses air in the second chamber 532, an air mass is emitted from the second chamber 532 into the compartment 2 through the outlet 533. The gaseous constituent flows from the first chamber 531 into the second chamber 532 through the communication part 535 by an operation of the compressing portion 534.

The compressing portion 534 has a box shape, and is movable in a front-and-rear direction. The compressing portion 534 has a predetermined dimension in the front-and-rear direction, and separates the inner space of the case 530 into a front space and a rear space. The second chamber 532 corresponds to the front space, and the first chamber 531 corresponds to the rear space. When the compressing portion 534 is moved toward the first chamber 531, the compressing portion 534 compresses air in the first chamber 531. When the compressing portion 534 is moved toward the second chamber 532, the compressing portion 534 compresses air in the second chamber 532.

The communication part 535 is positioned outside of the case 530, and has a passage for making the first chamber 531 and the second chamber 532 to communicate with each other. The communication part 535 has a first aperture 536 for communicating with the first chamber 531, and a second aperture 537 for communicating with the second chamber 532.

Figure 35A:
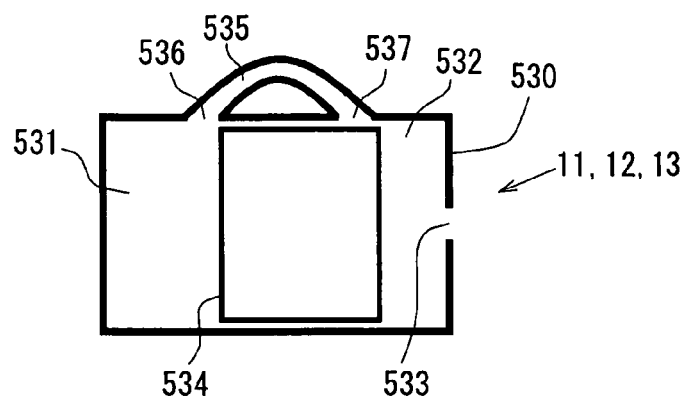
FIG. 35A is a schematic diagram showing a gaseous constituent supply device according to the 14th embodiment.

As shown in FIG. 35A, the volume of the second chamber 532 is made to be the smallest by the compressing portion 534, after the air mass is emitted. The compressing portion 534 does not close the first aperture 536, and closes the second aperture 537. Therefore, the first chamber 531 and the second chamber 532 do not communicate with each other through the communication part 535.

Figure 35B:
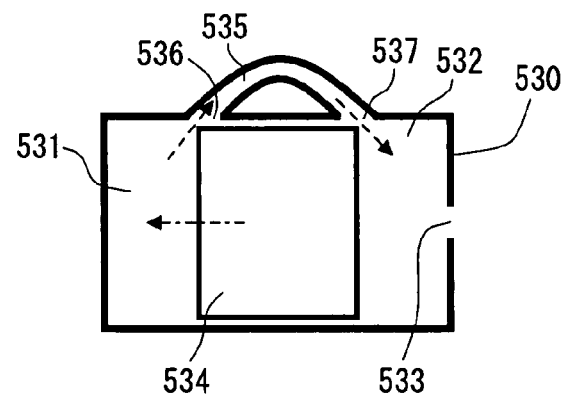
FIG. 35B is a schematic diagram showing the device in which a gaseous constituent is supplied to a second chamber.

Then, in order to compress air in the first chamber 531, the supply ECU 100 controls the compressing portion 534 to move in a chained arrow direction shown in FIG. 35B. At this time, a pressure in the first chamber 531 is increased, and a part of the first aperture 536 and a part of the second aperture 537 are open. Therefore, the gaseous constituent is pushed out of the first chamber 531 to the communication part 535 through the first aperture 536, and passes through the second aperture 537 to the second chamber 532, as shown of a dashed arrow in FIG. 35B.

When the compressing portion 534 compresses air in the first chamber 531, the gaseous constituent in the first chamber 531 is supplied to the second chamber 532. Therefore, a new air mass can be prepared to be emitted. At the same time, because a pressure in the second chamber 532 is decreased, air (i.e., air in the compartment 2) outside of the case 530 can be sucked into the second chamber 532 through the outlet 533.

Figure 35C:
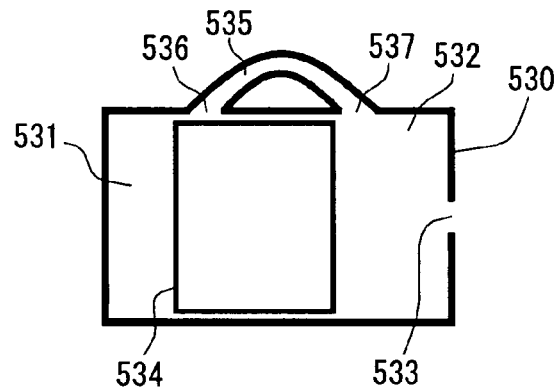
FIG. 35C is a schematic diagram showing the device before an air mass is emitted.

As shown in FIG. 35C, a volume of the first chamber 531 is made to be the smallest by the compressing portion 534, just before the air mass is emitted. The compressing portion 534 does not close the second aperture 537, and closes the first aperture 536. Therefore, the first chamber 531 and the second chamber 532 do not communicate with each other through the communication part 535.

Figure 33:
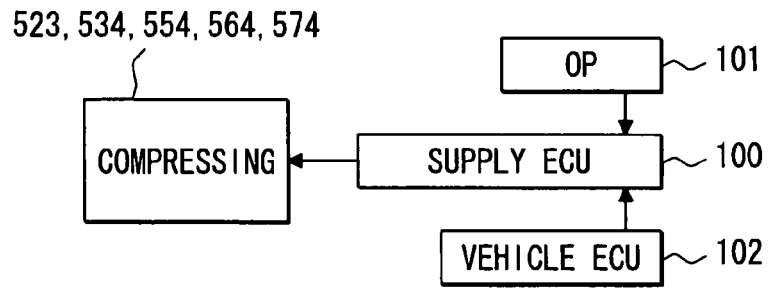
FIG. 33 is a block diagram showing a construction of the device of FIG. 32.
Figure 35D:
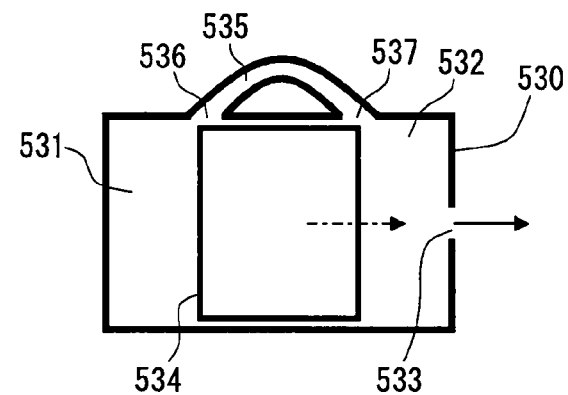
FIG. 35D is a schematic diagram showing the device in which the air mass is emitted.

Then, in order to compress air in the second chamber 532, the supply ECU 100 of FIG. 33 controls the compressing portion 534 to move in a chained arrow direction shown in FIG. 35D. That is, the compressing portion 534 is moved toward the outlet 533. At this time, because the volume of the second chamber 532 is instantaneously decreased, the air mass is emitted from the second chamber 532 into the compartment 2 through the outlet 533. Then, the air mass diffuses around the occupant 3, 4 such that the gaseous constituent in the air mass can be supplied to the occupant 3, 4. At this time, a part of the first aperture 536 and a part of the second aperture 537 are closed.

The air mass can be successively supplied to the occupant 3, 4 by repeating the operations of the compressing portion 534 shown in FIGS. 35A-35D. The device 11, 12, 13 has a simple structure without any supplying portion for supplying the gaseous constituent to the second chamber 532. That is, the device 11, 12, 13 has the case 530 and the compressing portion 534 separating the inner space of the case 530 into the first chamber 531 and the second chamber 532. In these series of the operations of the compressing portion 534, the apertures 536, 537 are not fully opened at the same time. That is, at least one of a part of the first aperture 536 and a part of the second aperture 537 is closed.

Another gaseous constituent supply device in the 14th embodiment will be described with reference to FIGS. 36A-36D. The device includes a shutter 541 for opening and closing the outlet 533 in the case 540. Other parts in the case 540 are made similar to those in the case 530.

Figure 36A:
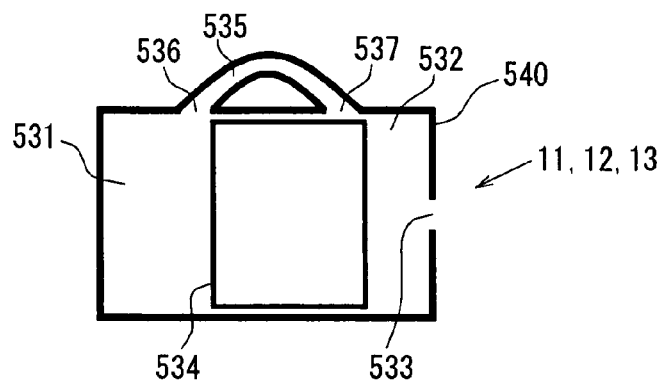
FIG. 36A is a schematic diagram showing another device.
Figure 36B:
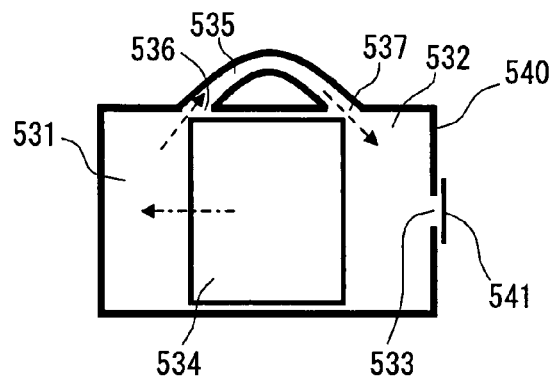
FIG. 36B is a schematic diagram showing the device in which a gaseous constituent is supplied to a second chamber.
Figure 36C:
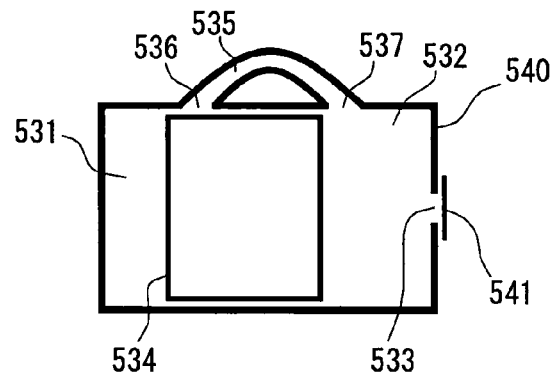
FIG. 36C is a schematic diagram showing the device before an air mass is emitted.
Figure 36D:
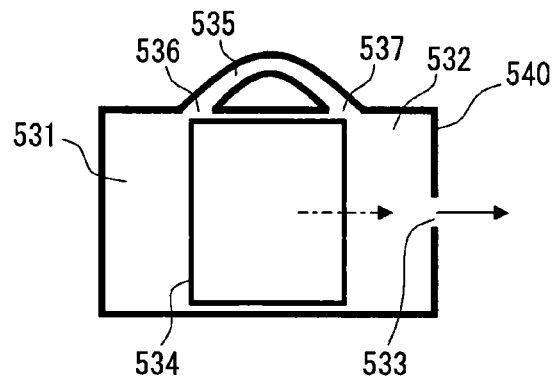
FIG. 36D is a schematic diagram showing the device in which the air mass is emitted, according to the 14th embodiment.

As shown in FIGS. 36B and 36C, the shutter 541 closes the outlet 533, after air in the compartment 2 is sufficiently sucked into the second chamber 532. Therefore, air can be prevented from leaking from the second chamber 532 into the compartment 2.

Specifically, in order to compress air in the first chamber 531, the supply ECU 100 controls the compressing portion 534 to move in a chained arrow direction shown in FIG. 36B. At this time, a pressure in the first chamber 531 is increased, and a part of the first aperture 536 and a part of the second aperture 537 are open. Therefore, the gaseous constituent is pushed out of the first chamber 531 into the communication part 535 through the first aperture 536, and passes through the second aperture 537 into the second chamber 532, as shown of a dashed arrow in FIG. 36B. At the same time, because a pressure in the second chamber 532 is decreased, outside air (i.e., air in the compartment 2) can be sucked into the second chamber 532 through the outlet 533. Then, the supply ECU 100 controls the shutter 541 to close the outlet 533, after air is sufficiently sucked from the compartment 2 into the second chamber 532.

The supply ECU 100 controls the compressing portion 534 such that the apertures 536, 537 are not fully opened at the same time. That is, at least one of a part of the first aperture and a part of the second aperture is closed. In this case, when air in the second chamber 532 is compressed, air in the second chamber 532 can be restricted from leaking from the second chamber 532. Further, when air in the first chamber 531 is compressed, the gaseous constituent can be appropriately supplied to the second chamber 532 from the first chamber 532.

Further, the shutter 541 closes the outlet 533 such that the gaseous constituent does not flow into the compartment 2, after the gaseous constituent is supplied to the second chamber 532 from the first chamber 531. In this case, leak of the gaseous constituent from the second chamber 532 can be reduced.

15th Embodiment

A gaseous constituent supply device 11, 12, 13 in a 15th embodiment will be described with reference to FIGS. 37A and 37B. An arrangement position and a control of the device 11, 12, 13 in the 15th embodiment are approximately similar to those in the 13th embodiment shown in FIGS. 32 and 33.

The device 11, 12, 13 includes a case 550. An emitting outlet 533, through which an air mass is emitted, is provided in a front face of the case 550. An inner space of the case 550 is separated into a first chamber 531 and a second chamber 532. The second chamber 532 communicates with the outlet 533, and the first chamber 531 is positioned at a rear side of the case 550. The first chamber 531 holds a predetermined gaseous constituent therein. The device 11, 12, 13 further has a communication part 535 and a compressing portion 554. The communication part 535 makes the first chamber 531 and the second chamber 532 to communicate with each other, and the compressing portion 554 changes a volume of the first chamber 531 or the second chamber 532.

The first chamber 531 and the second chamber 532 are separated by the compressing portion 554. The gaseous constituent in the first chamber 531 is sent to the second chamber 532 through the communication part 535 by an operation of the compressing portion 554.

The first chamber 531 holds the predetermined gaseous constituent in advance, and the compressing portion 554 changes a volume of the first chamber 531. The gaseous constituent is in a volatile state, and the first chamber 531 is filled with the volatile gaseous constituent. Usually, the gaseous constituent is sealed in the first chamber 531 by the compressing portion 554.

The second chamber 532 is filled with air sucked from the compartment 2 through the outlet 533, and the compressing portion 534 changes a volume of the second chamber 532. When the compressing portion 554 compresses air in the second chamber 532, an air mass is emitted from the second chamber 532 to the compartment 2 through the outlet 533. Further, the gaseous constituent flows from the first chamber 531 into the second chamber 532 through the communication part 535 by an operation of the compressing portion 554.

The compressing portion 554 includes a board 552 crossing the inner space of the case 550, a magnet 551 on the board 552, and a coil 553. The coil 553 surrounds the magnet 551 and the board 552. The compressing portion 540 is actuated by a moving-coil method, for example. The magnet 551 and the coil 553 can be insulated from the case 550 made of resin. The board 552 is thin, and made of a hard material, in order to reduce noise.

The magnet 551 may be fixed to the board 552 by adhesive, or the magnet 551 may be integrated with the board 552. Thereby, the magnet 551 is movable together with the board 552, and endurance performance against reciprocative movements is better.

The inner space of the case 550 is separated into a front space and a rear space by the board 552. The front space corresponds to the second chamber 532, and the rear space corresponds to the first chamber 531. The board 552 compresses air in the first chamber 531, when the supply ECU 100 controls the board 552 to move toward the rear side by a magnetic force and an electromagnetic force. The board 552 compresses air in the second chamber 532, when the supply ECU 100 of FIG. 33 controls the board 552 to move toward the front side by the magnetic force and the electromagnetic force.

When a voltage is applied to the compressing portion 554 from an in-vehicle battery, for example, the board 552 is moved toward the front side or the rear side by the electromagnetic force, because a current passes through the coil 553. When the voltage is appropriately controlled, the board 552 can be instantaneously moved. Due to the instantaneous movement of the board 552, a volume of the second chamber 532 is instantaneously decreased. Thereby, air containing the gaseous constituent in the second chamber 532 is compressed, and a part of the air is emitted to the compartment 2 through the outlet 533. By performing these operations instantaneously, the air containing the gaseous constituent in the second chamber 532 is formed into the air mass, and the air mass is emitted toward the compartment 2 as a fluid mass, e.g., air vortex ring or sphere.

The communication part 535 has a passage for making the first chamber 531 and the second chamber 532 to communicate with each other, and is disposed outside of the case 550. The communication part 535 has a first aperture 536 for communicating with the first chamber 531 and a second aperture 537 for communicating with the second chamber 532. Further, a first door 555 opens and closes the first aperture 536, and a second door 556 opens and closes the second aperture 537. The door 555, 556 prevents a reverse-flow of air.

Next, operation of the device will be described. As shown of a chained arrow in FIG. 37A, the supply ECU 100 controls the compressing portion 554 to move toward the rear side in order to compress air in the first chamber 531. At this time, a pressure in the first chamber 531 is increased, and the doors 555, 556 are moved about a supporting axis so as to open the communication part 535. Then, the gaseous constituent flows from the first chamber 531 into the second chamber 532 through the communication part 535, as shown of a dashed arrow in FIG. 37A.

Figure 37A:
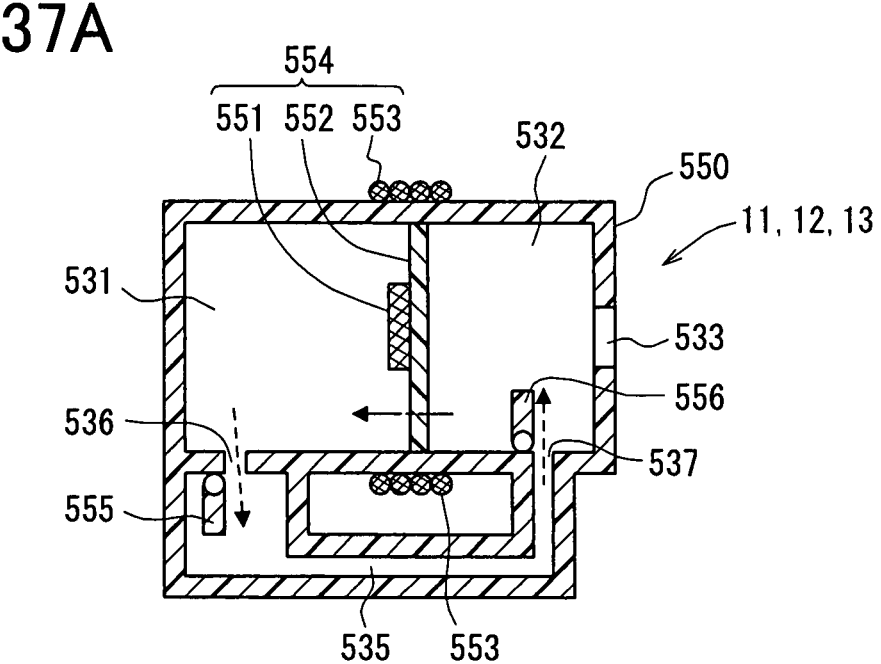
FIG. 37A is a cross-sectional view showing a gaseous constituent supply device according to a 15th embodiment before an air mass is emitted.
Figure 37B:
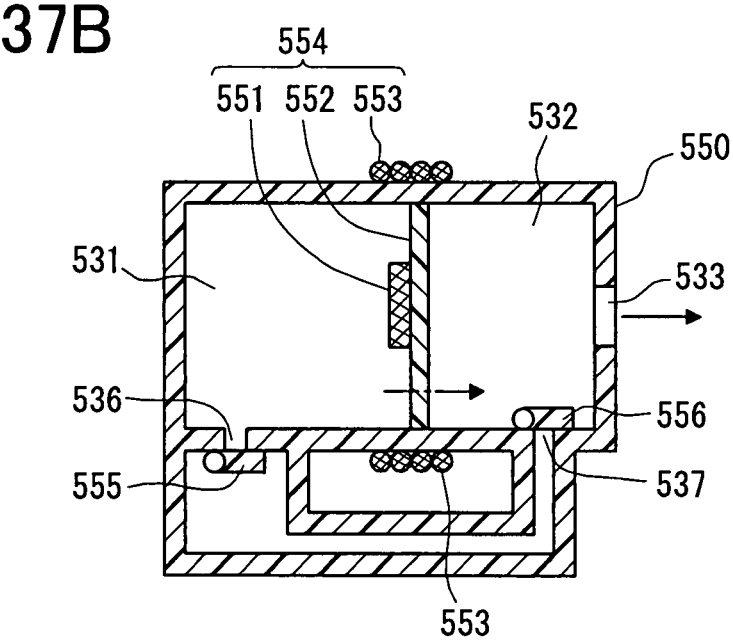
FIG. 37B is a cross-sectional view showing the device in which the air mass is emitted.

Thereafter, as shown of a chained arrow in FIG. 37B, the supply ECU 100 controls the compressing portion 554 to move toward the front side in order to compress air in the second chamber 532. At this time, a part of air in the second chamber 532 is emitted to the compartment 2 as the air mass through the outlet 533, due to an instantaneous decrease in a volume of the second chamber 532. The air mass diffuses around the occupant 3, 4 so as to provide the gaseous constituent to the occupant 3, 4. In addition, as shown in FIG. 37B, the first door 555 closes the first aperture 536, and the second door 556 closes the second aperture 537, in order to prevent air from moving from the second chamber 532 into the first chamber 531 through the communication part 535.

According to the 15th embodiment, the air mass can be successively supplied to the occupant 3, 4 by repeating the above-described operations shown in FIGS. 37A and 37B. The device has a simple structure without any supplying portion for supplying the gaseous constituent to the second chamber 532. Further, because the compressing portion 554 is driven by the electromagnetic force, the air mass can be successively or timely emitted.

The device 11, 12, 13 includes the first and second doors 555, 556. When the compressing portion 554 compresses air in the first chamber 531, the communication part 535 is opened by the doors 555, 556. Therefore, necessary amount of the gaseous constituent can be supplied to the second chamber 532. In contrast, when the compressing portion 554 compresses air in the second chamber 532, the communication part 535 is closed by the doors 555, 556. Therefore, the air mass can be secured to be emitted, because leak of air from the second chamber 532 can be reduced.

16th Embodiment

A gaseous constituent supply device 11, 12, 13 in a 16th embodiment will be described with reference to FIGS. 38A-39. An arrangement position and a control of the device are approximately similar to those in the 13th embodiment shown in FIGS. 32 and 33.

Figure 38A:
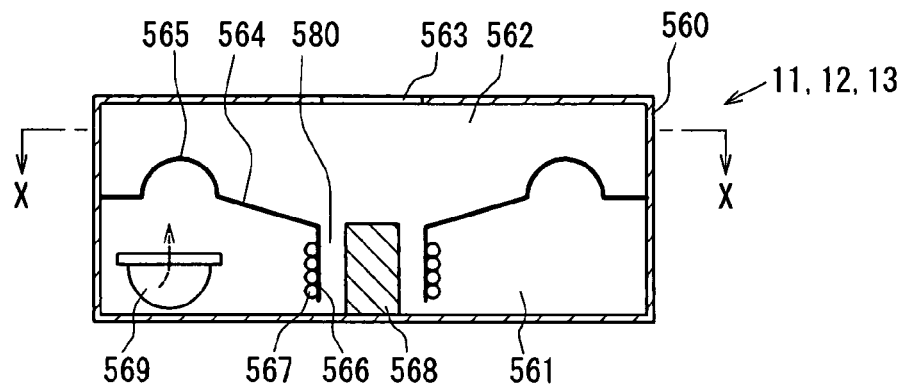
FIG. 38A is a schematic diagram showing a gaseous constituent supply device according to a 16th embodiment.

As shown in FIG. 38A, the device includes a case 560, and an emitting outlet 563 is provided in a front face of the case 560. An air mass is emitted from the case 560 into the compartment 2 through the outlet 563. An inner space of the case 560 is separated into a first chamber 561 and a second chamber 562. The second chamber 562 communicates with the outlet 563, and the first chamber 561 is positioned at a rear side of the case 560. The first chamber 561 holds a predetermined gaseous constituent therein. The device further includes a clearance 580 (communication part) and a movable portion 564 in the case 560. The communication part 580 makes the first chamber 561 and the second chamber 562 to communicate with each other, and the movable portion 564 changes a volume of the first chamber 561 or the second chamber 562.

The first chamber 561 and the second chamber 562 are provided in an inner space of the case 560 through the movable portion 564. That is, the first chamber 561 and the second chamber 562 are separated by the movable portion 564.

The movable portion 564 is controlled by the supply ECU 100. When the movable portion 564 is moved toward the outlet 563 (front side), a volume of the second chamber 562 is decreased. In contrast, when the movable portion 564 is moved toward the rear side, a volume of the first chamber 561 is decreased. At the same time, the gaseous constituent in the first chamber 561 is moved from the first chamber 561 to the second chamber 562 through the communication part 580. Then, when the movable portion 564 is moved toward the front side, air in the second chamber 562 is emitted to the compartment 2 through the outlet 563.

The first chamber 561 holds the predetermined gaseous constituent in advance, and the volume of the first chamber 561 can be changed by the movable portion 564. The gaseous constituent is stored in a reserving portion 569 constructed with a cartridge, for example. The gaseous constituent is gradually discharged from the reserving portion 569, and the first chamber 561 is filled with the gaseous constituent in a volatile state. In addition, the reserving portion 569 can be renewed when its content becomes less.

The second chamber 562 is filled with air sucked from the compartment 2 through the outlet 563, and the volume of the second chamber 562 can be changed by the movable portion 564. When air in the second chamber 562 is compressed, an air mass is emitted to the compartment 2 through the outlet 563. When the movable portion 564 is moved toward the rear side, the gaseous constituent flows from the first chamber 561 into the second chamber 562 through the communication part 580.

A compressing unit crosses the inner space of the case 560, and includes the movable portion 564, an elastic deformation portion 565, a pipe 566, a coil 567 and a magnet 568. The movable portion 564 and the elastic deformation portion 565 are integrated into a board shape. The magnet 568 generates a magnetic force. The coil 567 is twisted around the pipe 566 so as to surround the magnet 568. The compressing unit is actuated by a moving-coil method, for example.

The magnet 568 is disposed on an inner rear face of the case 560 so as to cross the inner space of the case 560. The communication part 580 has a predetermined clearance between an inner surface of the pipe 566 and an outer surface of the magnet 568. The predetermined clearance can be kept, even when the pipe 566 is moved in the front-and-rear direction. The pipe 566 is moved by the electromagnetic force, which is generated by the coil 567 and the magnet 568. The communication part 580 makes the first chamber 561 and the second chamber 562 to communicate with each other.

The pipe 566 is made of resin, e.g., polycarbonate. The coil 567 is made of a conductive material, e.g., enamel. The magnet 568 is fixed to the inner rear face of the case 560 by an adhesive, or integrated with the inner rear face of the case 560.

The movable portion 564 extends perpendicular to the front-and-rear direction. An outer end of the movable portion 564 is fixed to an inner surface of the case 560, and an inner end of the movable portion 564 is integrated with a front side end of the pipe 566. The movable portion 564 forms a border between the first chamber 561 and the second chamber 562, and crosses the inner space of the case 560.

Figure 39:
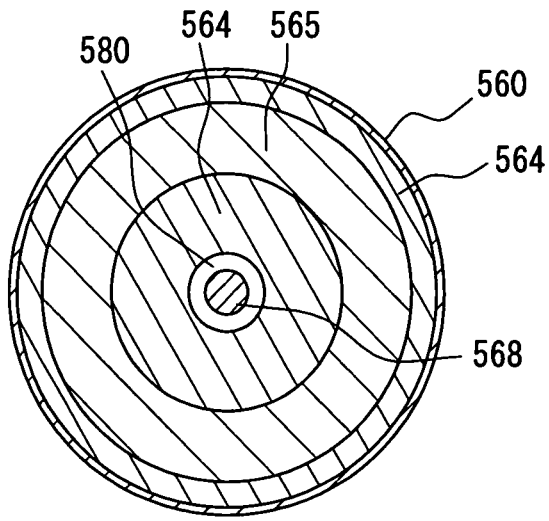
FIG. 39 is a cross-sectional view taken along line X-X in FIG. 38A.

As shown in FIG. 39, the elastic deformation portion 565 is provided in the movable portion 564, and integrated with the movable portion 564. The movable portion 564 integrated with the elastic deformation portion 565 is fixed to the inner surface of the case 560. The elastic deformation portion 565 is disposed between the magnet 568 and the inner surface of the case 560, similarly to the movable portion 564. The movable portion 564 can be stably moved, because the elastic deformation portion 565 is elastically deformed so as to correspond to the movement of the movable portion 564.

The movable portion 564 is made of a thin and hard board, for example. Thus, operation noise of the movable portion 564 can be reduced. Further, the elastic deformation portion 565 is made of much harder material than the movable portion 564. Thus, the movable portion 564 can be more stably moved, due to the elastic deformation portion 565.

In addition, the communication part 580 extends from the first chamber 561 to the second chamber 562 at an approximately center part of the inner space of the case 560, as shown in FIG. 39. The communication part 580 is positioned to face the outlet 563. The case 560 has an approximately round shape, as shown in FIG. 39. The case 560 may have the front-and-rear dimension, which is smaller than a diameter of the case 560, for example, as shown in FIG. 38A. That is, the case 560 may have a cylinder shape, and a height of the cylinder shape may be smaller than a diameter of the cylinder shape.

A control of the compressing unit by the supply ECU 100 of FIG. 33 will be described below. When a voltage is applied to the coil 567 from an in-vehicle battery, an electromagnetic force is generated by the coil 567, because a current passes through the coil 567. The electromagnetic force displaces the pipe 566 in the front-and-rear direction. Thus, the movable portion 564 is moved toward the first chamber 561 or the second chamber 562.

When the voltage applied to the coil 567 is appropriately controlled, the movable portion 564 can be instantaneously moved in the front-and-rear direction. Due to the movement of the movable portion 564, a volume of the second chamber 562 is instantaneously decreased. Thereby, air containing the gaseous constituent in the second chamber 562 is compressed, and a part of the air is emitted to the compartment 2 through the outlet 563. By performing these operations instantaneously, the air containing the gaseous constituent in the second chamber 562 is emitted to the compartment 2 as a fluid mass, e.g., air vortex ring or sphere.

Next, an operation of the device will be described below. The supply ECU 100 controls the compressing unit to compress air in the second chamber 562, in order to emit an air mass toward the occupant 3, 4 in the compartment 2. Specifically, when electricity is supplied to the coil 567, the electromagnetic force is generated by the coil 567. Thereby, the pipe 566 is instantaneously moved toward the outlet 563. That is, as shown of an outline arrow in FIG. 38B, the pipe 566 and the movable portion 564 are moved toward the outlet 563.

At this time, air containing the gaseous constituent in the second chamber 562 is emitted to the compartment 2 through the outlet 563 as the air mass, due to the instantaneous decrease in the volume of the second chamber 562. The air mass diffuses in the compartment 2 so as to supply the gaseous constituent to the occupant 3, 4.

Thereafter, the supply ECU 100 controls the compressing unit to compress air in the first chamber 561. Thereby, air is sucked from the compartment 2 into the second chamber 562, and the gaseous constituent in the first chamber 561 is moved to the second chamber 562, in order to prepare a new air mass emission. Specifically, electricity is supplied to the coil 567, and the electromagnetic force is generated by the coil 567. Therefore, the pipe 566 and the movable portion 564 are instantaneously moved toward the rear side, as shown of an outline arrow in FIG. 38C.

At this time, air containing the gaseous constituent is moved from the first chamber 561 to the second chamber 562 through the communication part 580, because a pressure in the first chamber 561 is increased. At the same time, air is sucked into the second chamber 562 from the compartment 2, because a negative pressure is formed in the second chamber 562.

Figure 38B:
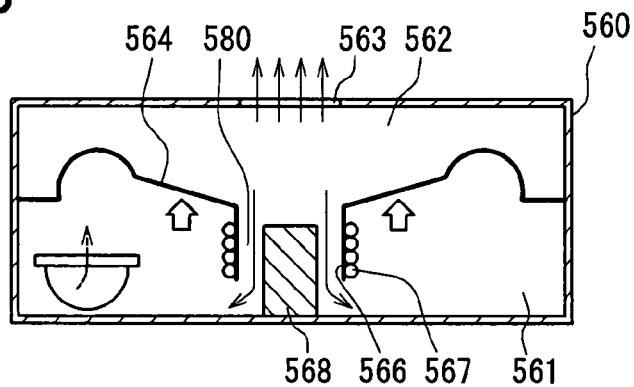
FIG. 38B is a schematic diagram showing the device in which an air mass is emitted.
Figure 38C:
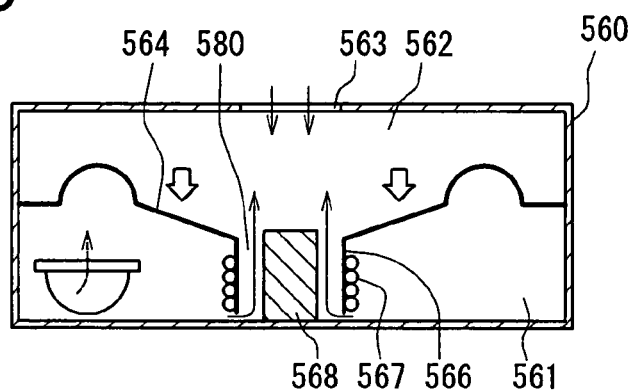
FIG. 38C is a schematic diagram showing the device in which a gaseous constituent is supplied to a second chamber.

According to the 16th embodiment, the air mass can be successively supplied to the occupant 3, 4 by repeating the operations shown in FIGS. 38B and 38C. The device has a simple structure without any supplying portion for supplying the gaseous constituent to the second chamber 562. Further, because the compressing unit is driven by the electromagnetic force, the air mass can be successively or timely emitted.

The device 11, 12, 13 includes the first chamber 561 holding the predetermined gaseous constituent, the second chamber 562, from which the air mass containing the gaseous constituent is emitted, and the communication part 580 for making the first chamber 561 and the second chamber 562 to communicate with each other. Further, the device 11, 12, 13 includes the movable portion 564 separating the inner space of the case 560 into the first chamber 561 and the second chamber 562. The movable portion 564 is moved toward the outlet 563 to decrease the volume of the second chamber 562, or moved toward the rear side to decrease the volume of the first chamber 561. When the movable portion 564 is moved toward the rear side, the gaseous constituent is supplied to the second chamber 562 from the first chamber 561 through the communication part 580.

According to the 16th embodiment, a size of the device 11, 12, 13 can be reduced. Further, the number of parts of the device can be reduced, because any supplying portion for supplying the gaseous constituent to the second chamber 562 is not needed.

Further, the movable portion 564 can be moved by the electromagnetic force, which is generated by the coil 567 and the magnet 568. The communication part 580 is constructed with the clearance between the magnet 568 and the movable portion 564. Therefore, an arrangement space for the communication part 580 and the compressing unit can be effectively reduced. Thus, the size of the device 11, 12, 13 can be much reduced.

Further, because the movable portion 564 is positioned to surround the magnet 568, the electromagnetic force can stably move the movable portion 564.

Further, because the movable portion 564 is supported by the elastic deformation portion 565, the communication part 580 can have a constant clearance between the magnet 568 and the movable portion 564. Thus, air can stably flow from the first chamber 561 to the second chamber 562.

Further, when the communication part 580 is positioned at an approximately center part of the case 560, the gaseous constituent can be effectively diffused in the second chamber 562, because the communication part 580 extends in the front-and-rear direction at the approximately center part of the case 560.

Further, when the communication part 580 is positioned to face the outlet 563, the gaseous constituent can be appropriately gathered adjacent to the outlet 563, because the position of the communication part 580 corresponds to that of the outlet 563.

17th Embodiment

A 17th embodiment will be described with reference to FIGS. 40A-41. A gaseous constituent supply device 11, 12, 13 includes a sealing portion 583 capable of sealing the communication part 580 of the 16th embodiment. When emission of the air mass is stopped, the sealing portion 583 closes the communication part 580. Other parts in the 17th embodiment may be made similar to the 16th embodiment.

Figure 41:
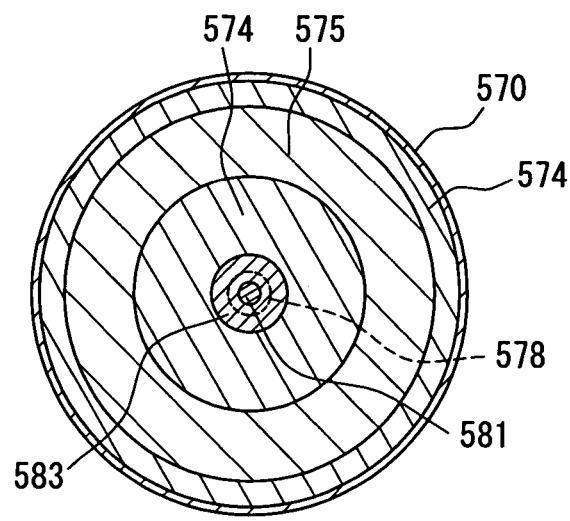
FIG. 41 is a cross-sectional view taken along line Y-Y in FIG. 40A.
Figure 40A:
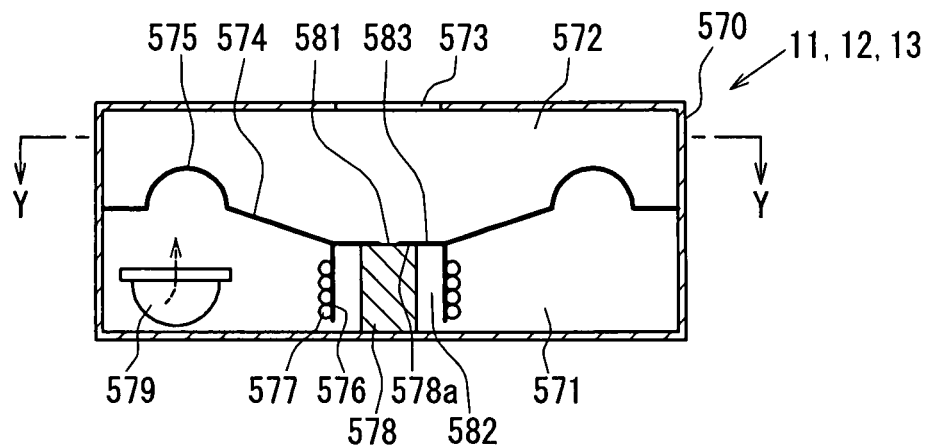
FIG. 40A is a schematic diagram showing a gaseous constituent supply device according to a 17th embodiment.
Figure 40B:
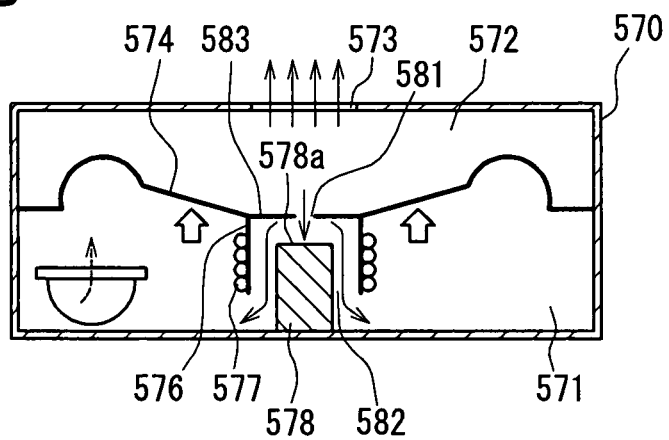
FIG. 40B is a schematic diagram showing the device in which an air mass is emitted.

Specifically, as shown in FIGS. 40A-41, the device includes the sealing portion 583 for sealing a communication part 582 between the magnet 578 and the pipe 576. The sealing portion 583 extends from a point connecting the pipe 576 and the movable portion 574 to cover a front side end 578a of the magnet 578. The front side end 578a of the magnet 578 has a face approximately perpendicular to an axis direction of the cylinder-shaped magnet 578. That is, the face of the front side end 578a of the magnet 578 is approximately perpendicular to a moving direction of the pipe 576 and the sealing portion 583. The sealing portion 583 has a hole 581 for making the communication part 582 and the second chamber 572 to communicate with each other. When the supply ECU 100 stops emission of the air mass into the compartment 2, the sealing portion 583 makes the first chamber 571 and the second chamber 572 not to communicate with each other.

The communication between the first chamber 571 and the second chamber 572 can be stopped by making the sealing portion 583 in contact with the magnet 578. The sealing portion 583 is made of a flexible material having a high sealing performance, e.g., urethane or elastomer.

In addition, as shown in FIG. 41, the communication part 582 and the hole 581 are positioned at an approximately center part of the inner space of the case 570. FIG. 41 shows the inner space of the device 11, 12, 13. Further, the communication part 582 and the hole 581 are positioned to face the outlet 573.

Next, operation of the device 11, 12, 13 will be described. The supply ECU 100 of FIG. 33 controls the compressing unit to compress air in the second chamber 572, in order to emit the air mass toward the occupant 3, 4 in the compartment 2. Specifically, electricity is supplied to the coil 577, and an electromagnetic force generated by the coil 577 instantaneously moves the pipe 576 toward the outlet 573. Thus, the pipe 576 and the movable portion 574 are moved toward the outlet 573, as shown of an outline arrow in FIG. 40B.

At this time, air containing the gaseous constituent in the second chamber 572 is emitted as the air mass to the compartment 2 through the outlet 573, due to an instantaneous decrease in a volume of the second chamber 572. Then, the air mass is diffused around the occupant 3, 4 so as to supply the gaseous constituent to the occupant 3, 4.

Next, the supply ECU 100 controls the compressing unit to compress air in the first chamber 571. Thus, air is sucked into the second chamber 572 from the compartment 2, and the gaseous constituent is sent from the first chamber 571 to the second chamber 572, in order to prepare a new air mass emission toward the occupant 3, 4 in the compartment 2. Specifically, electricity is supplied to the coil 577, and an electromagnetic force generated by the coil 577 instantaneously moves the pipe 576 toward the rear side. Thus, the pipe 576 and the movable portion 574 are moved toward the rear side, as shown of an outline arrow in FIG. 40C.

At this time, air containing the gaseous constituent in the first chamber 571 flows into the second chamber 572 through the communication part 582 and the hole 581, due to an increase of a pressure in the first chamber 571. At the same time, air is sucked into the second chamber 572 through the outlet 573 from the compartment 2, due to a negative pressure in the second chamber 572.

Figure 40C:
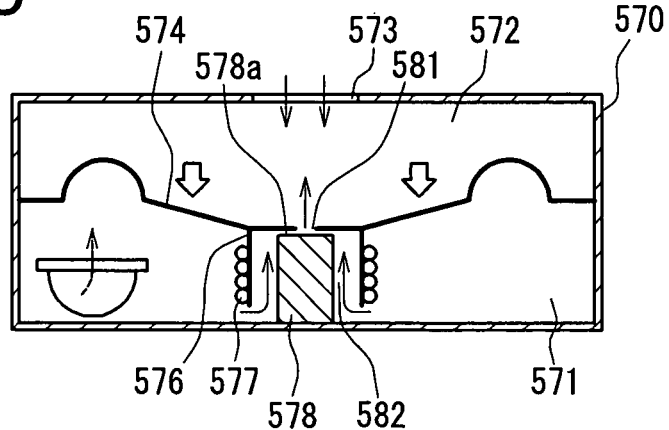
FIG. 40C is a schematic diagram showing the device in which a gaseous constituent is supplied to a second chamber.
Figure 42:
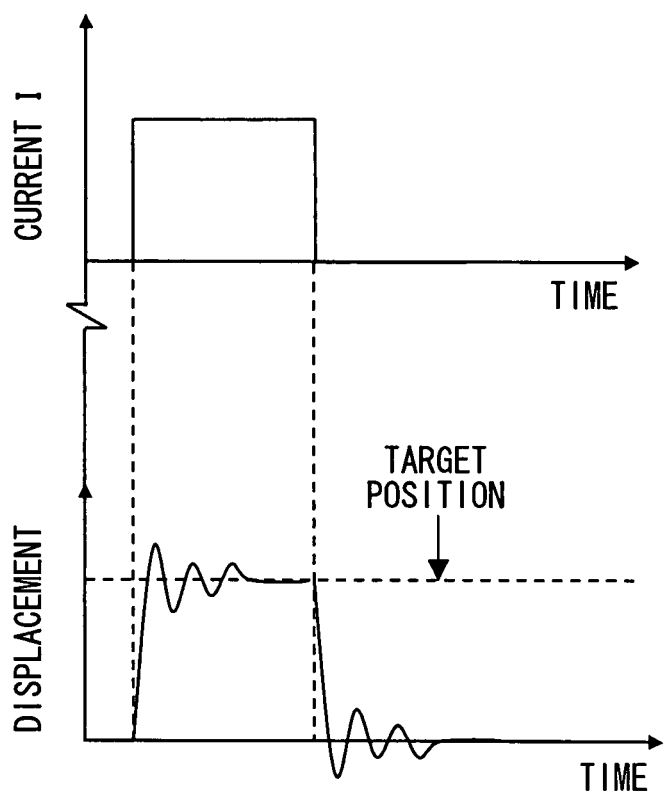
FIG. 42 is a graph showing a relationship between a time and a current, and a displacement of a compressive member of a conventional gaseous constituent supply device.

Further, when the supply ECU 100 stops the emission of the air mass, that is when the emission of the air mass is stopped for a predetermined period, the pipe 576 is much moved toward the first chamber 571, compared with a state shown in FIG. 40C.

Thereby, the sealing portion 583 is made in contact with the front side end 578a of the magnet 578. Thus, the communication between the first chamber 571 and the second chamber 572 is totally closed, because the front side end 578a of the magnet 578 is in contact with a back face of the sealing portion 583.

According to the 17th embodiment, the air mass can be successively supplied to the occupant 3, 4. The device has a simple construction without any additional supplying member or any additional sealing member.

The sealing portion 583 stops the communication between the first chamber 571 and the second chamber 572, when the emission of the air mass is stopped. Therefore, the gaseous constituent can be restricted from leaking from the first chamber 571. Further, refilling of the gaseous constituent in the reserving portion 579 or exchanging the cartridge in the reserving portion 579 can be reduced, because the gaseous constituent is not used in waste.

The sealing portion 583 is made in contact with the magnet 578 in order to totally stop the communication between the first chamber 571 and the second chamber 572, when the emission of the air mass is stopped. In this case, the sealing portion 583 can be made with a simple structure, e.g., valve.

Further, the sealing portion 583 is in contact with a face perpendicular to a moving direction of the sealing portion 583, in order to stop the communication between the first chamber 571 and the second chamber 572. In this case, the moving direction of the sealing portion 583 and a direction of a sealing force are the same. Therefore, high sealing performance can be provided in the device. Furthermore, a sealing face of the sealing portion 583 is approximately parallel to a compression face of the movable portion 574. Therefore, energy loss is small, and the sealing performance is high.

(Modification)

In the above-described 13th to 17th embodiments, the supply ECU 100 is used only for controlling the compressing portion or the compressing unit. However, the supply ECU 100 may be included in another ECU for an air-conditioning apparatus, and in charge of the control of the compressing portion or the compressing unit.

The construction and the operation of the device 11, 12, 13 are not limited to the above example. For example, the device 11, 12, 13 may include a wave-shaped mechanism or a cam mechanism capable of moving in the front-and-rear direction between the first chamber 571 and the second chamber 572.

Other Embodiment

Any gaseous constituent supply device described in the above embodiments may be mounted to a railway vehicle, a boat, a ship or an airplane. Further, the device may be used in an interior of a house or building.

Such changes and modifications are to be understood as being within the scope of the present invention as defined by the appended claims.

What is claimed is:

1. A gaseous constituent supply device for supplying an air vortex ring containing a gaseous constituent, the device comprising:
   a first chamber holding the gaseous constituent therein, and having an opening, through which air containing the gaseous constituent is blown;
   a compressing portion for compressing air in the first chamber so as to blow air from the first chamber through the opening;
   a second chamber communicating with the first chamber through the opening, and
   a partition wall partitioning the first chamber and the second chamber from each other, wherein
   the second chamber holds the gaseous constituent therein, and has an emitting outlet provided opposite to the opening of the first chamber,
   the second chamber generates the air vortex ring by air blown from the first chamber through the opening while taking in the gaseous constituent,
   the second chamber emits the generated air vortex ring through the emitting outlet
   the opening of the first chamber is provided in the partition wall and is open to the second chamber,
   the emitting outlet of the second chamber is positioned opposite from the opening of the first chamber,
   the second chamber is a space defined between the partition wall and the emitting outlet;
   the opening of the first chamber has a first round shape,
   the emitting outlet of the second chamber has a second round shape, and
   the first round shape and the second round shape have approximately the same axis which is perpendicular to the partition wall.

2. The gaseous constituent supply device according to claim 1, wherein the compressing portion compresses air in the first chamber such that air blown from the first chamber through the opening takes in gaseous constituent in the second chamber adjacent to the blow air, when the air vortex ring is generated in the second chamber.

3. The gaseous constituent supply device according to claim 1, wherein the compressing portion compresses air in the first chamber such that air blown from the first chamber through the opening sucks the gaseous constituent in the second chamber, when the air vortex ring is generated in the second chamber.

4. The gaseous constituent supply device according to claim 1, wherein the first and second chambers are constructed with a case and the partition wall dividing an inner space of the case into the first and second chambers, and the emitting outlet is provided in a wall portion of the case.

5. The gaseous constituent supply device according to claim 1, wherein the emitting outlet has an aperture area, which is larger than that of the opening.

6. The gaseous constituent supply device according to claim 1, wherein the emitting outlet has an aperture dimension, which is larger than an external dimension of the air vortex ring generated in the second chamber.

7. The gaseous constituent supply device according to claim 3, wherein the partition wall is located to provide a communication part for making the first and second chambers communicate with each other, such that the gaseous constituent is supplied from the first chamber into the second chamber through the communication part.

8. The gaseous constituent supply device according to claim 7, wherein the communication part has an aperture area, which is smaller than that of the opening.

9. The gaseous constituent supply device according to claim 1, further comprising:

a gaseous constituent supplying portion for supplying the gaseous constituent to the second chamber.

10. The gaseous constituent supply device according to claim 9, wherein the gaseous constituent supplying portion further supplies the gaseous constituent to the first chamber.

11. The gaseous constituent supply device according to claim 1, wherein the second chamber generates the air vortex ring inside of the second chamber prior to emitting the generated air vortex ring.

12. The gaseous constituent supply device according to claim 1, wherein the gaseous constituent is a perfume component, the second chamber holds the perfume component therein which is supplied from the first chamber, and the air vortex ring is constructed of the air blown from the first chamber and the perfume component held in the second chamber.

13. The gaseous constituent supply device according to claim 1, wherein the compressing portion includes a pressing member movable within the first chamber which reduces a volume of said first chamber to compress the air in the first chamber.

14. The gaseous constituent supply device according to claim 1, wherein the opening through which air containing the gaseous constituent is blown generates the air vortex ring in the second chamber.

* * * * *